US012682992B1

(12) United States Patent

Tong et al.

(10) Patent No.: US 12,682,992 B1

(45) Date of Patent: Jul. 14, 2026

(54) EXTENSION OF USER INTERFACE BASED SOFTWARE INTEGRATION TO NEAR REAL TIME AND SINGLE SIGN ON

(71) Applicant: Siu Tong, Cary, NC (US)

(72) Inventors: Siu Tong, Cary, NC (US); Naveen Vangipurapu, Cary, NC (US)

( * ) Notice: Subject to any disclaimer, the term of this patent is extended or adjusted under 35 U.S.C. 154(b) by 248 days.

(21) Appl. No.: 18/378,112

(22) Filed: Dec. 7, 2023

Related U.S. Application Data

(63) Continuation-in-part of application No. 16/661,661, filed on Oct. 23, 2019, now Pat. No. 11,783,922.

(60) Provisional application No. 62/749,817, filed on Oct. 24, 2018.

(51) Int. Cl.
*G16H 10/60* (2018.01)
*H04L 9/40* (2022.01)
*H04L 67/02* (2022.01)

(52) U.S. Cl.
CPC ......... *G16H 10/60* (2018.01); *H04L 63/0815* (2013.01); *H04L 67/02* (2013.01)

(58) Field of Classification Search
CPC ...... G16H 10/60; H04L 63/0815; H04L 67/02
See application file for complete search history.

(56) References Cited

U.S. PATENT DOCUMENTS

| | | | |
|---|---|---|---|
| 8,595,206 B1 | 11/2013 | Ansari | |
| 2007/0192140 A1* | 8/2007 | Gropper | G06F 21/6245 |
| | | | 715/205 |
| 2012/0253801 A1 | 10/2012 | Santos-Lang | |
| 2013/0262396 A1 | 10/2013 | Kripalani | |
| 2014/0278542 A1* | 9/2014 | Fernandez | G16H 10/60 |
| | | | 705/3 |
| 2015/0278462 A1 | 10/2015 | Smoley | |
| 2017/0357759 A1 | 12/2017 | Stepaniuk | |
| 2018/0041515 A1* | 2/2018 | Gupta | G06F 21/53 |
| 2018/0121612 A1* | 5/2018 | Connely, IV | H04W 12/02 |
| 2019/0180862 A1* | 6/2019 | Wisser | G16H 30/40 |
| 2019/0304582 A1 | 10/2019 | Blumenthal | |
| 2019/0374292 A1 | 12/2019 | Barral | |
| 2021/0306323 A1* | 9/2021 | Suraparaju | H04L 67/10 |
| 2023/0023159 A1* | 1/2023 | Brodegard | G16H 40/67 |
| 2023/0148065 A1* | 5/2023 | David | G06F 21/45 |
| | | | 726/5 |
| 2023/0409352 A1* | 12/2023 | LaForge | G06F 3/04817 |
| 2024/0394412 A1* | 11/2024 | Shin | G06F 21/6263 |
| 2025/0077591 A1* | 3/2025 | Dang | G06F 16/9532 |

* cited by examiner

*Primary Examiner* — Fonya M Long
*Assistant Examiner* — Anthony Balaj
(74) *Attorney, Agent, or Firm* — ROARK IP

(57) ABSTRACT

A browser extension will provide an electronic health record (EHR) user with access to a button that can be clicked to launch a third-party application from the health information technology (IT) vendor. By clicking the button, the EHR user is able to directly log into the health vendor's third-party application without a need for entering credentials and also the EHR user logs into the same patient context as the patient the EHR user is accessing in the EHR system.

15 Claims, 37 Drawing Sheets

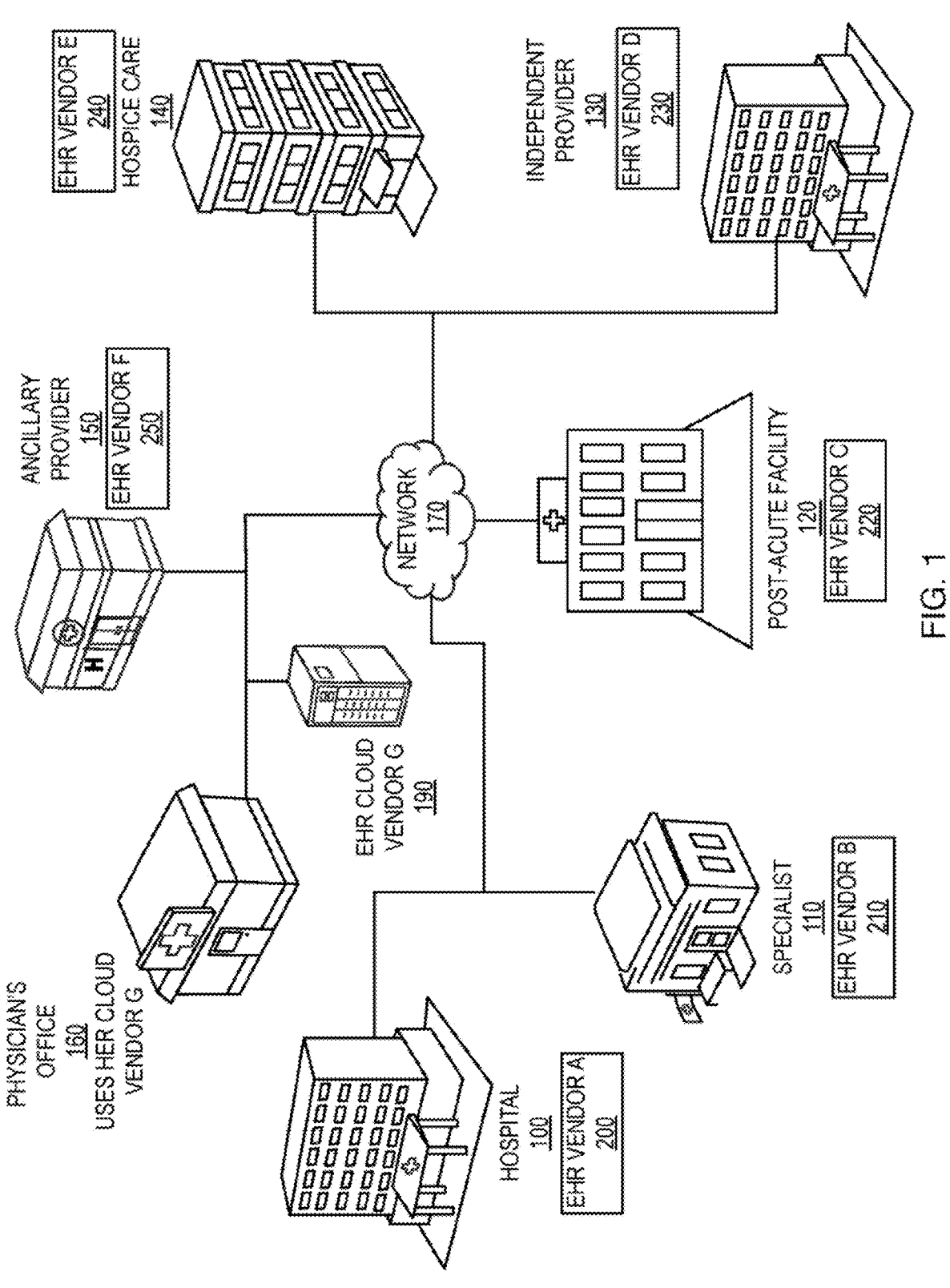
FIG. 1

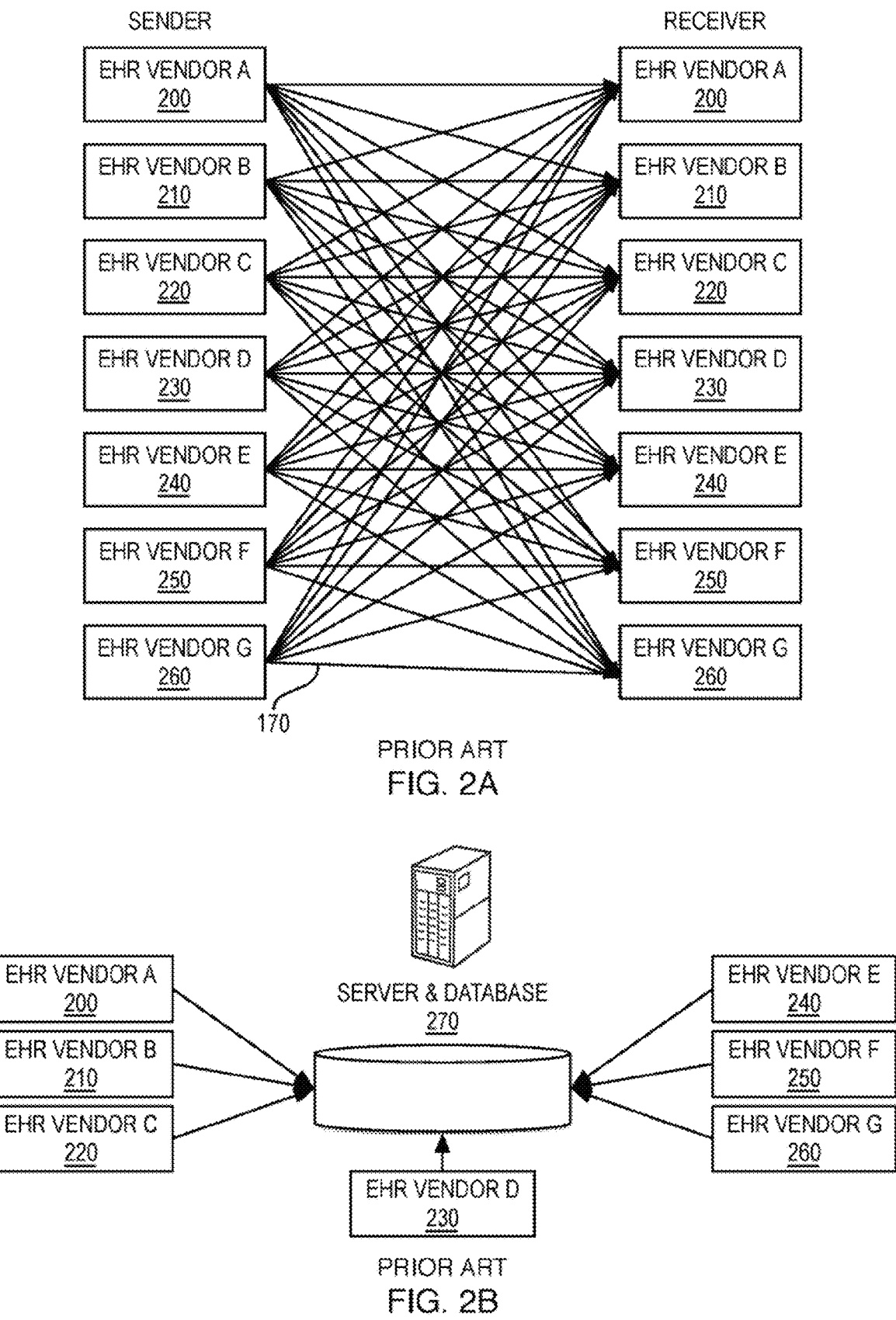
PRIOR ART
FIG. 2A
PRIOR ART
FIG. 2B

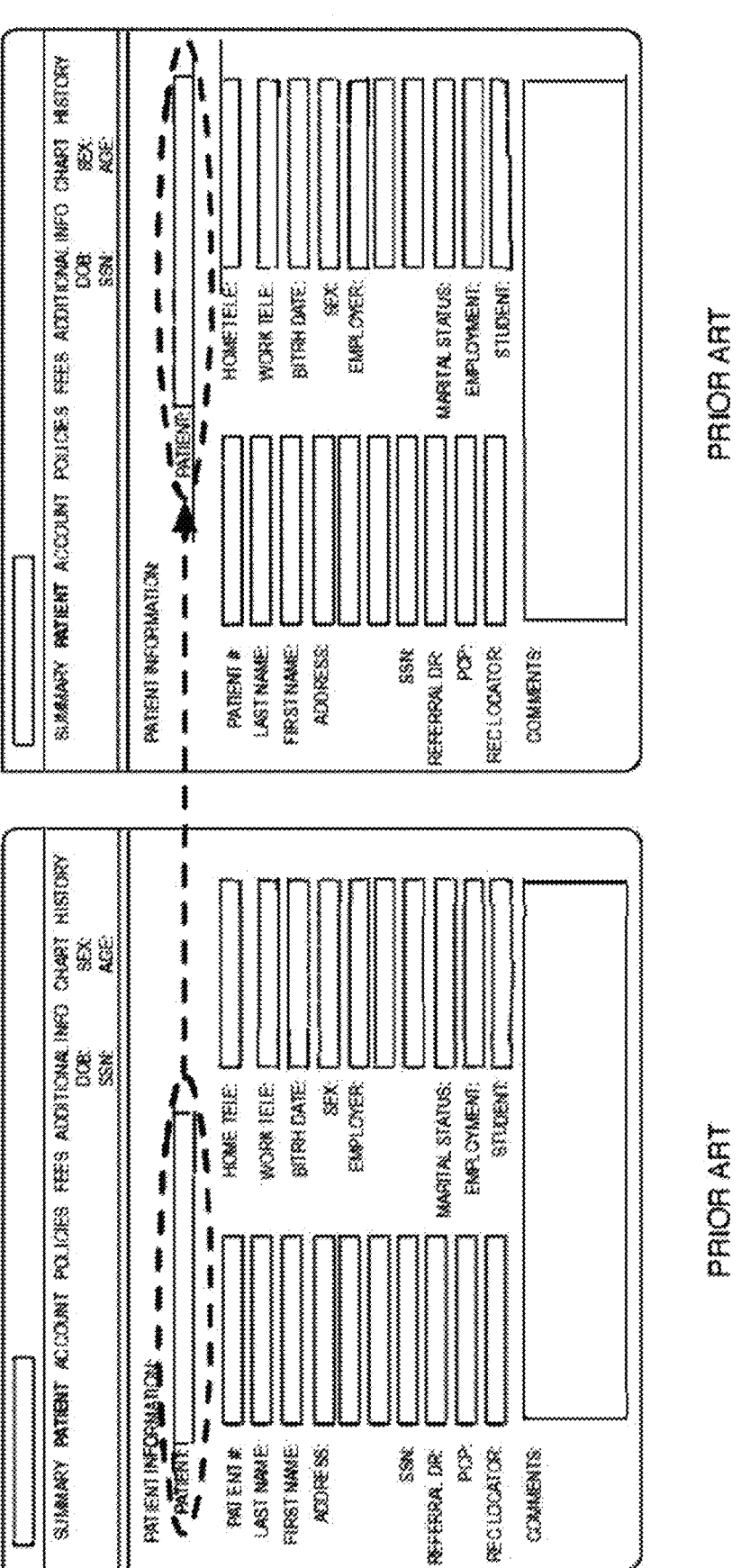
PRIOR ART
FIG. 2D
PRIOR ART
FIG. 2C

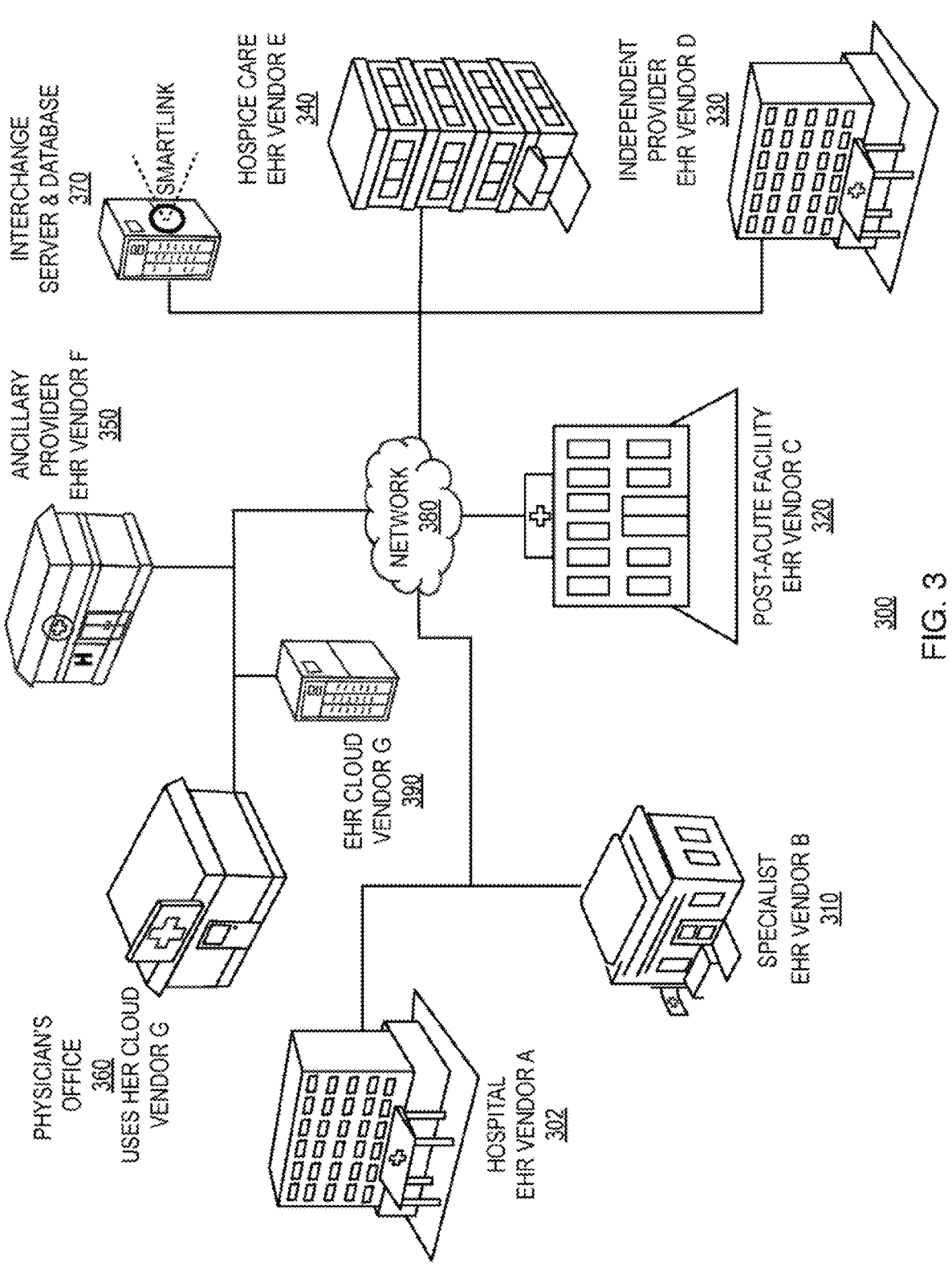
FIG. 3

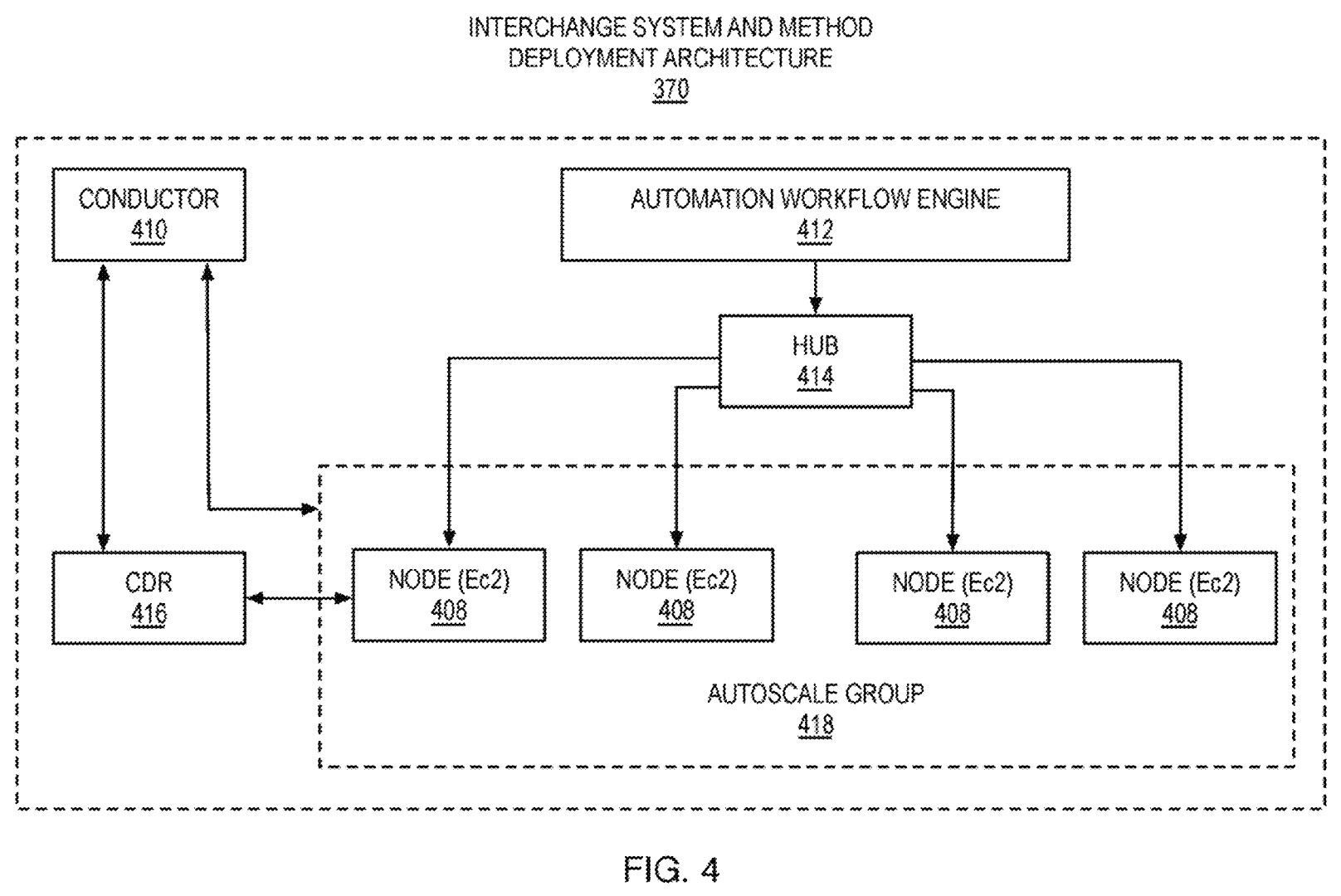

INTERCHANGE SYSTEM AND METHOD
DEPLOYMENT ARCHITECTURE
370

AUTOMATION WORKFLOW ENGINE
412

HUB
414

NODE (Ec2)
408

NODE (Ec2)
408

NODE (Ec2)
408

NODE (Ec2)
408

AUTOSCALE GROUP
418

CONDUCTOR
410

CDR
416

FIG. 4

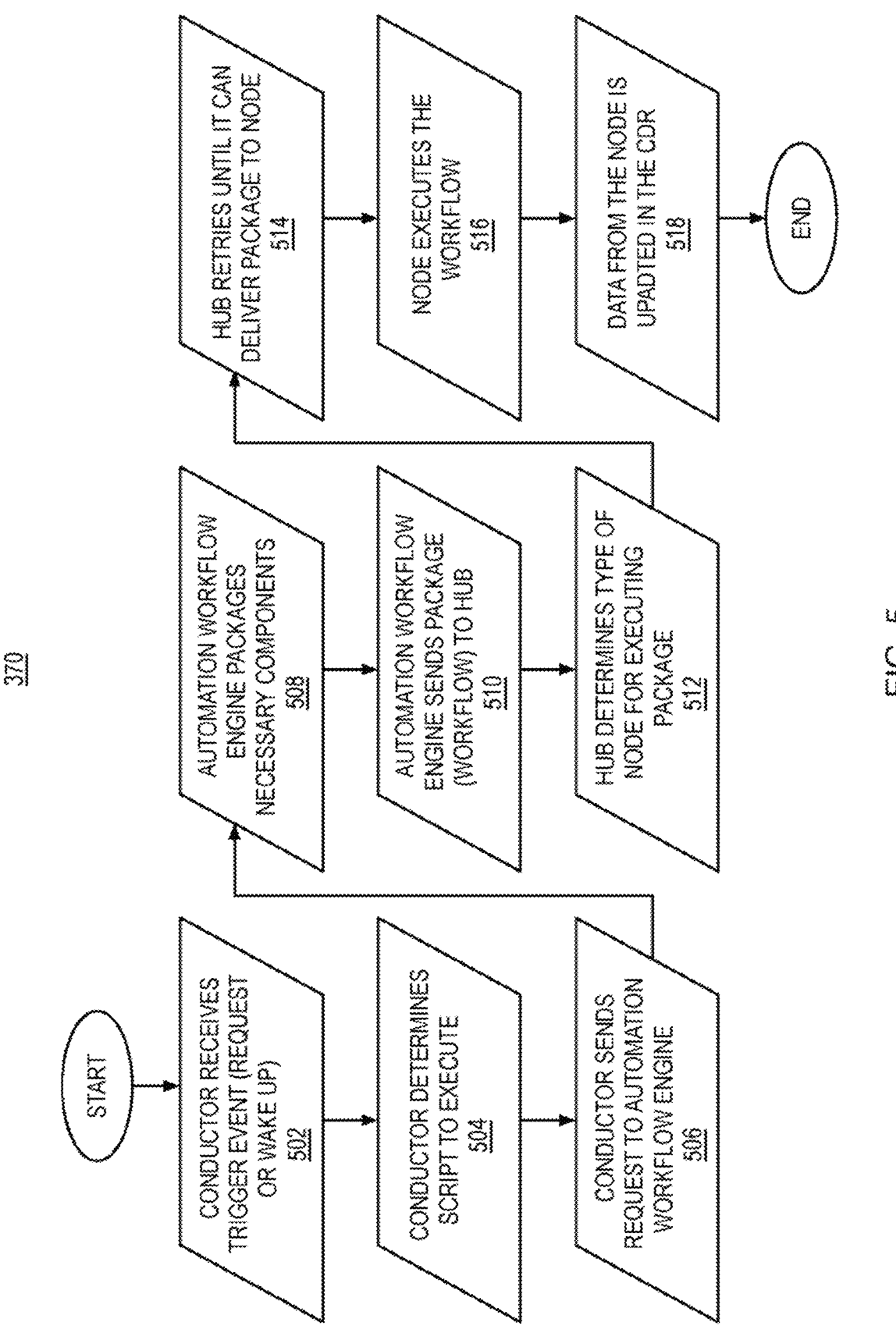
FIG. 5

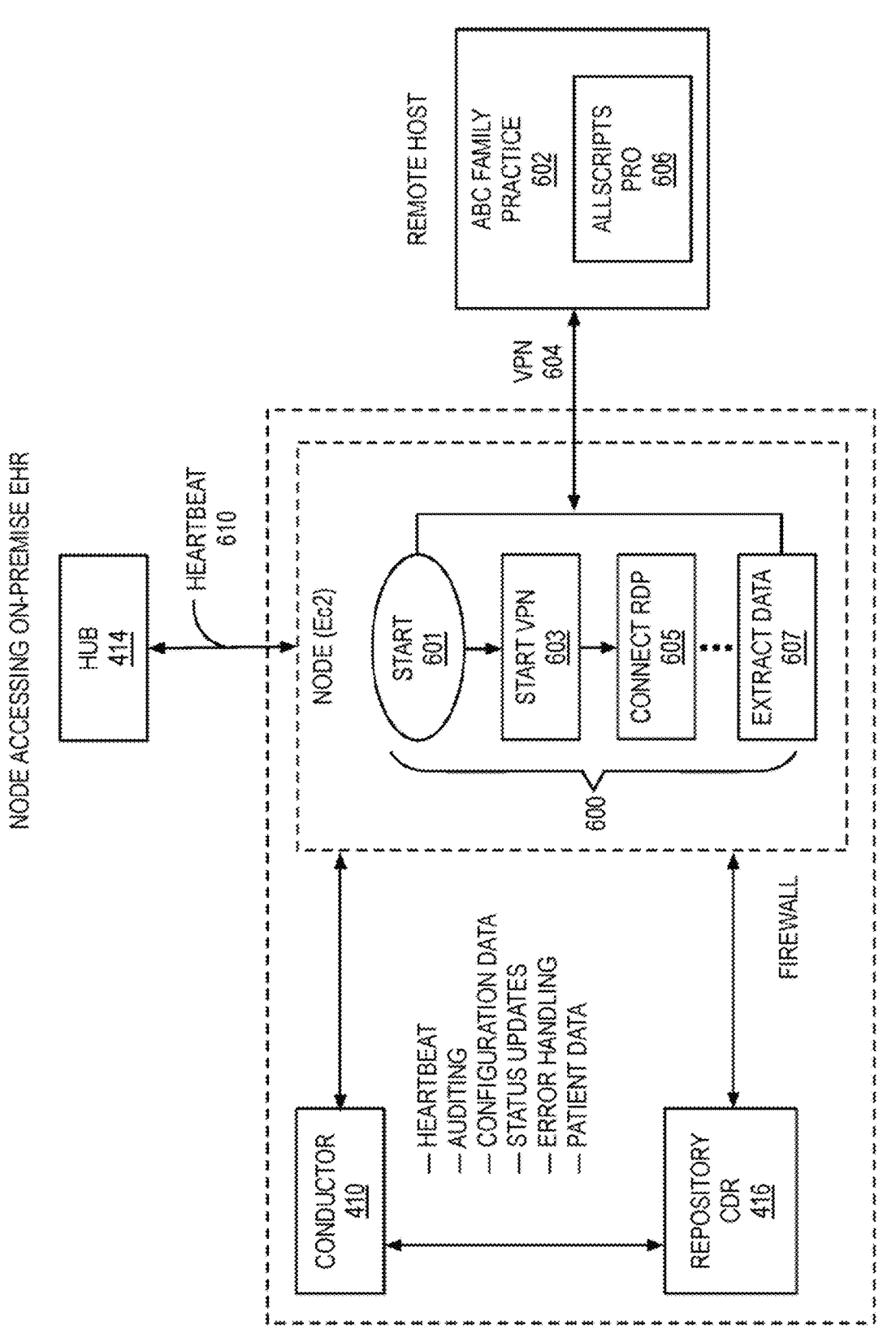
FIG. 6

FIG. 7

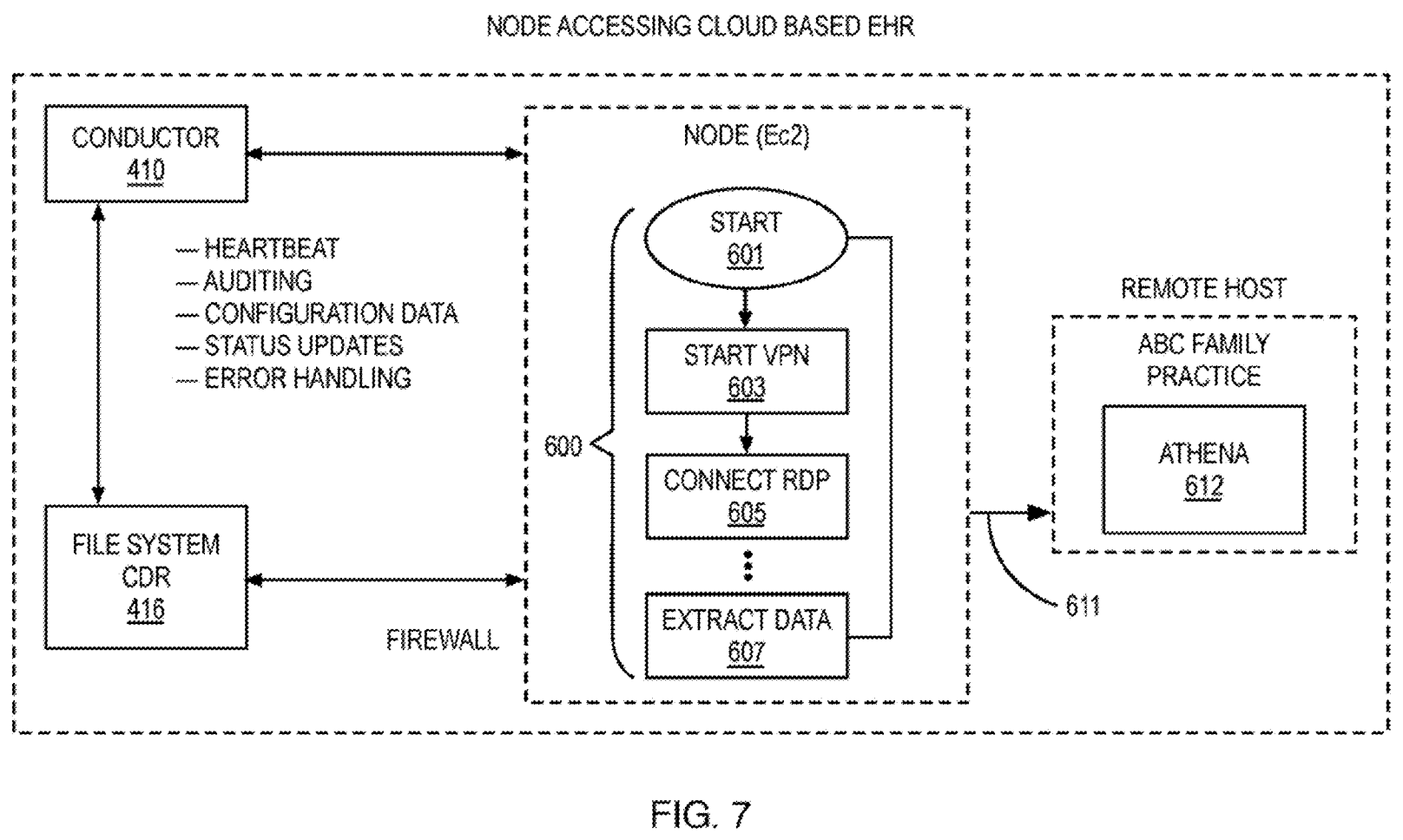

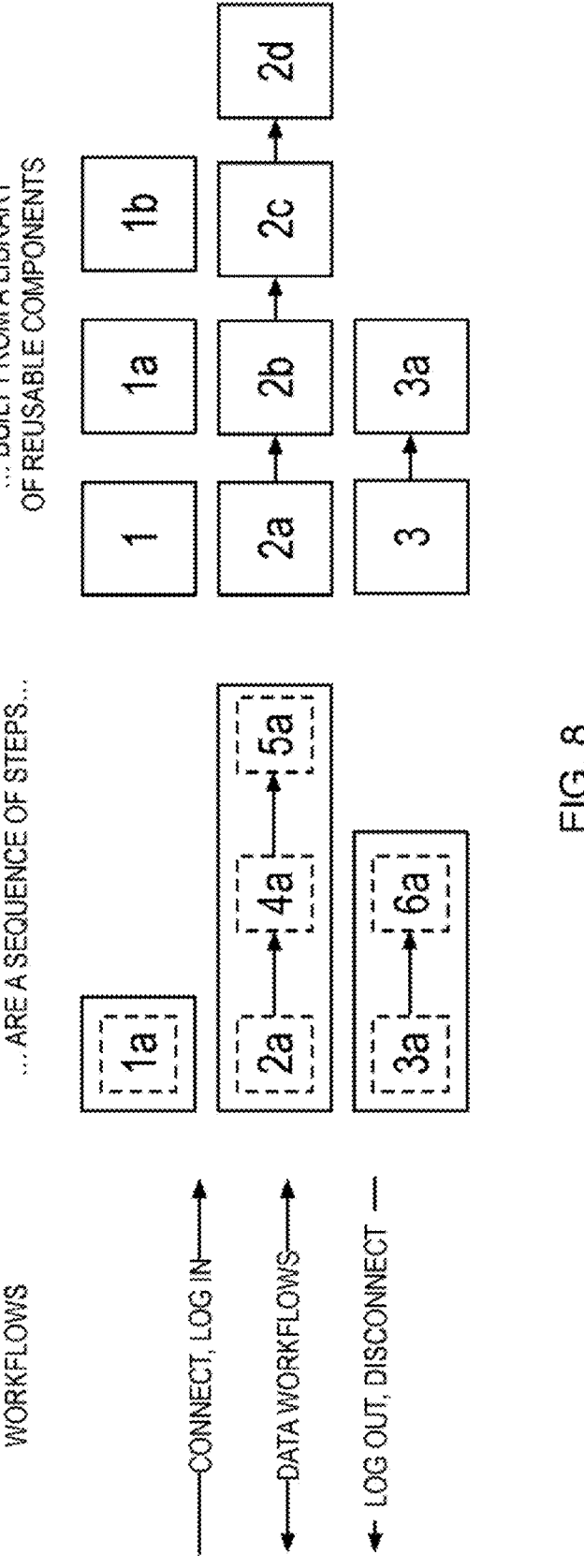
FIG. 8

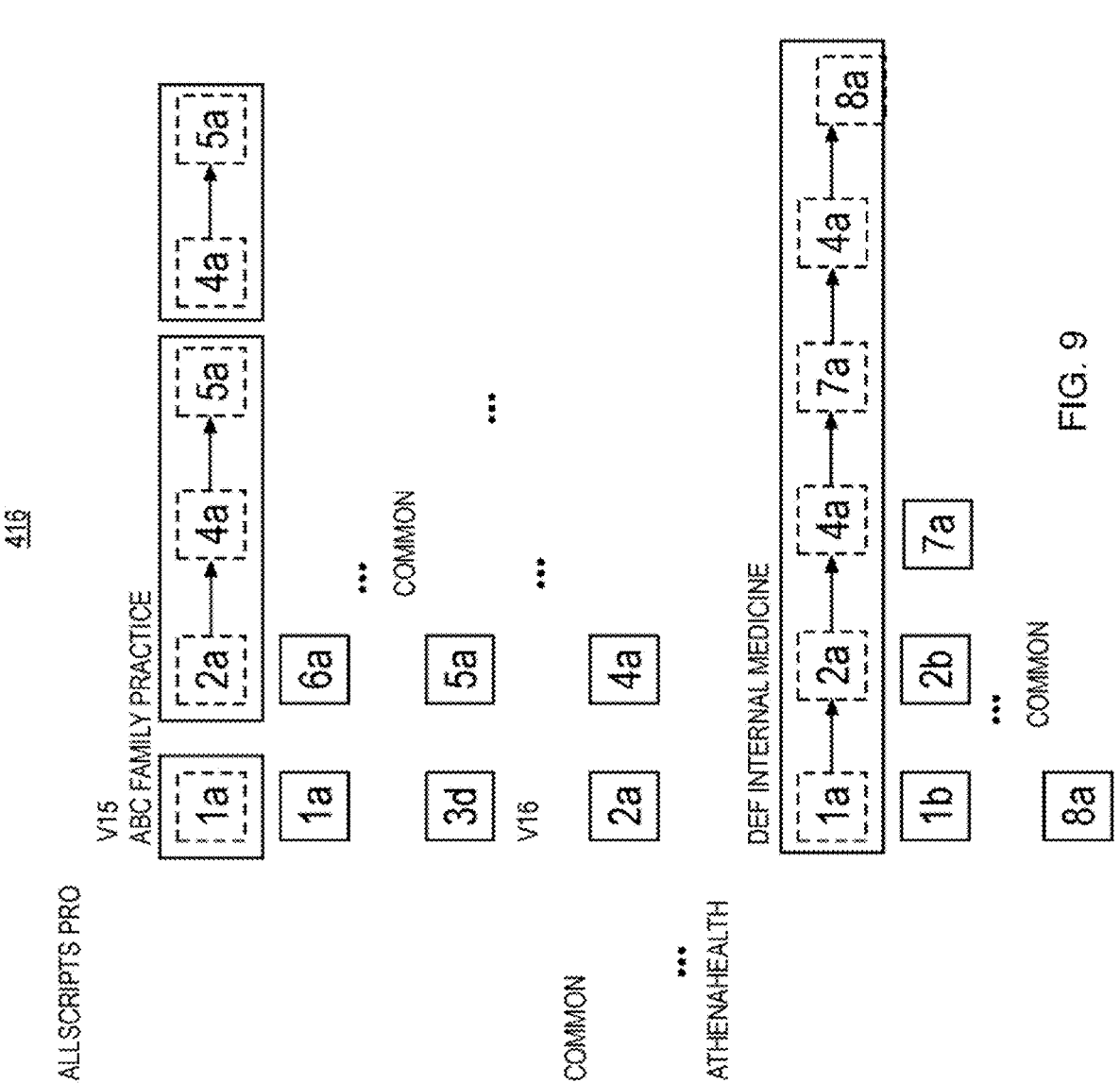
FIG. 9

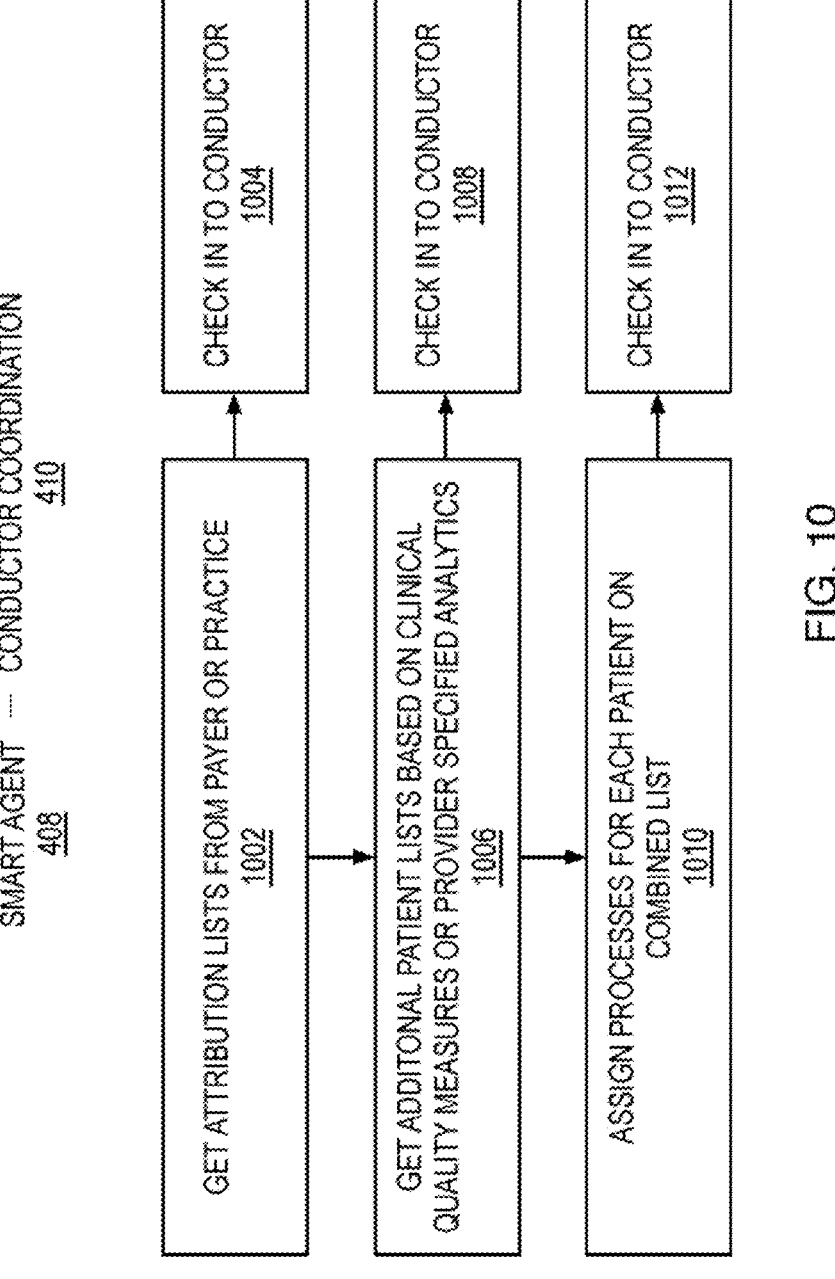
FIG. 10

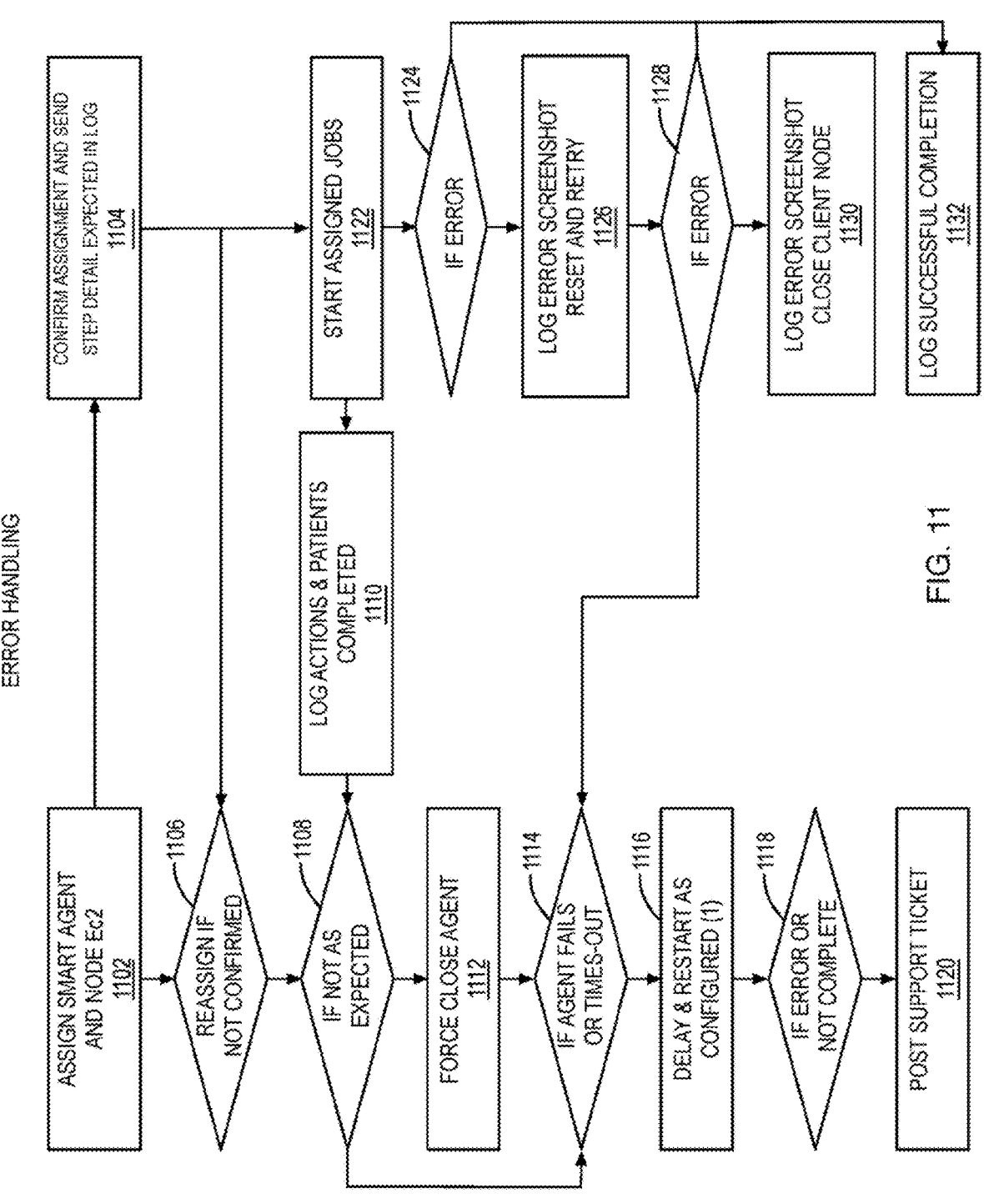

ERROR HANDLING

CONFIRM ASSIGNMENT AND SEND STEP DETAIL EXPECTED IN LOG
1104

START ASSIGNED JOBS
1122

IF ERROR
1124

LOG ERROR SCREENSHOT RESET AND RETRY
1126

IF ERROR
1128

LOG ERROR SCREENSHOT CLOSE CLIENT NODE
1130

LOG SUCCESSFUL COMPLETION
1132

LOG ACTIONS & PATIENTS COMPLETED
1110

ASSIGN SMART AGENT AND NODE Ec2
1102

REASSIGN IF NOT CONFIRMED
1106

IF NOT AS EXPECTED
1108

FORCE CLOSE AGENT
1112

IF AGENT FAILS OR TIMES-OUT
1114

DELAY & RESTART AS CONFIGURED (1)
1116

IF ERROR OR NOT COMPLETE
1118

POST SUPPORT TICKET
1120

FIG. 11

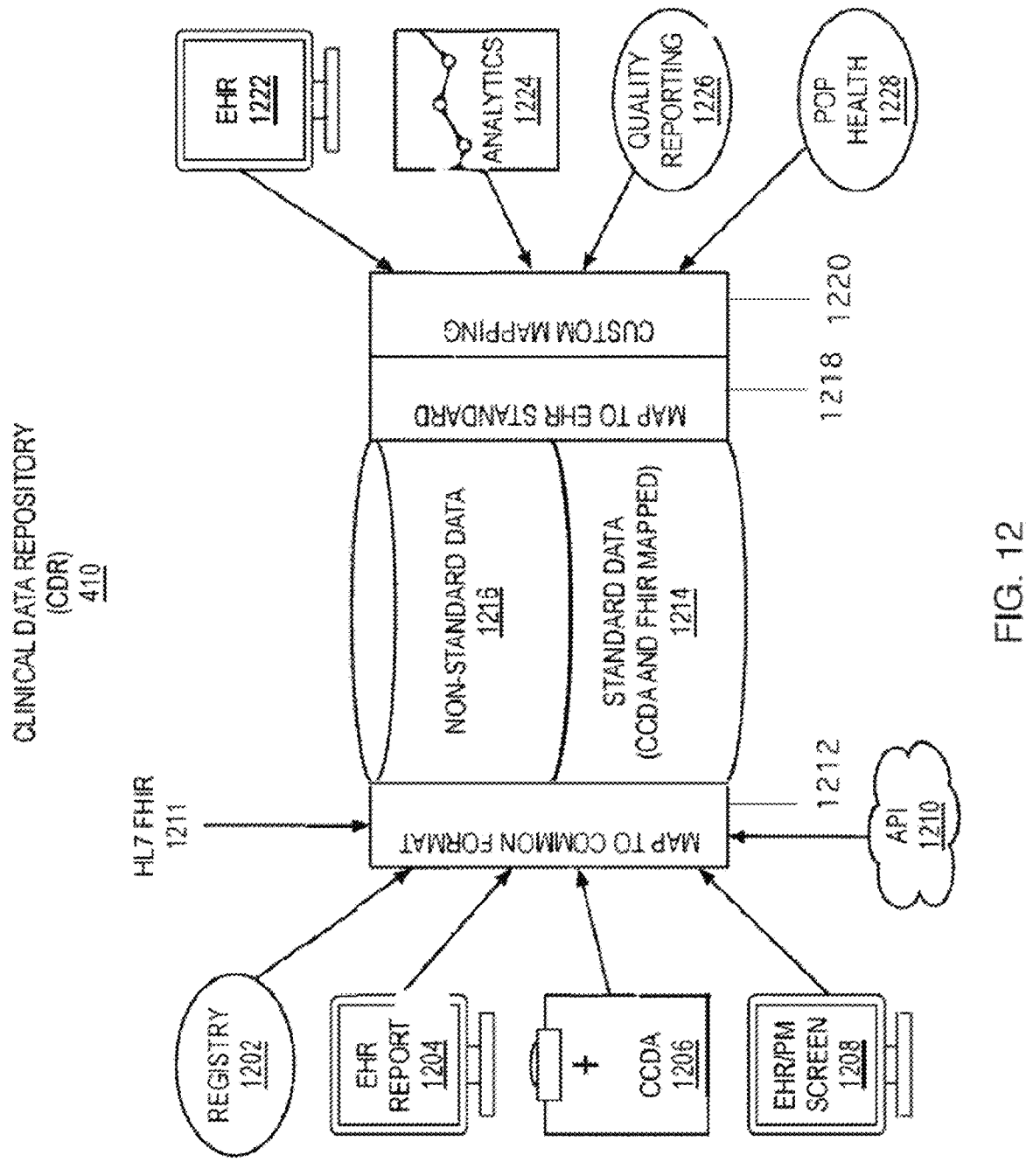
FIG. 12

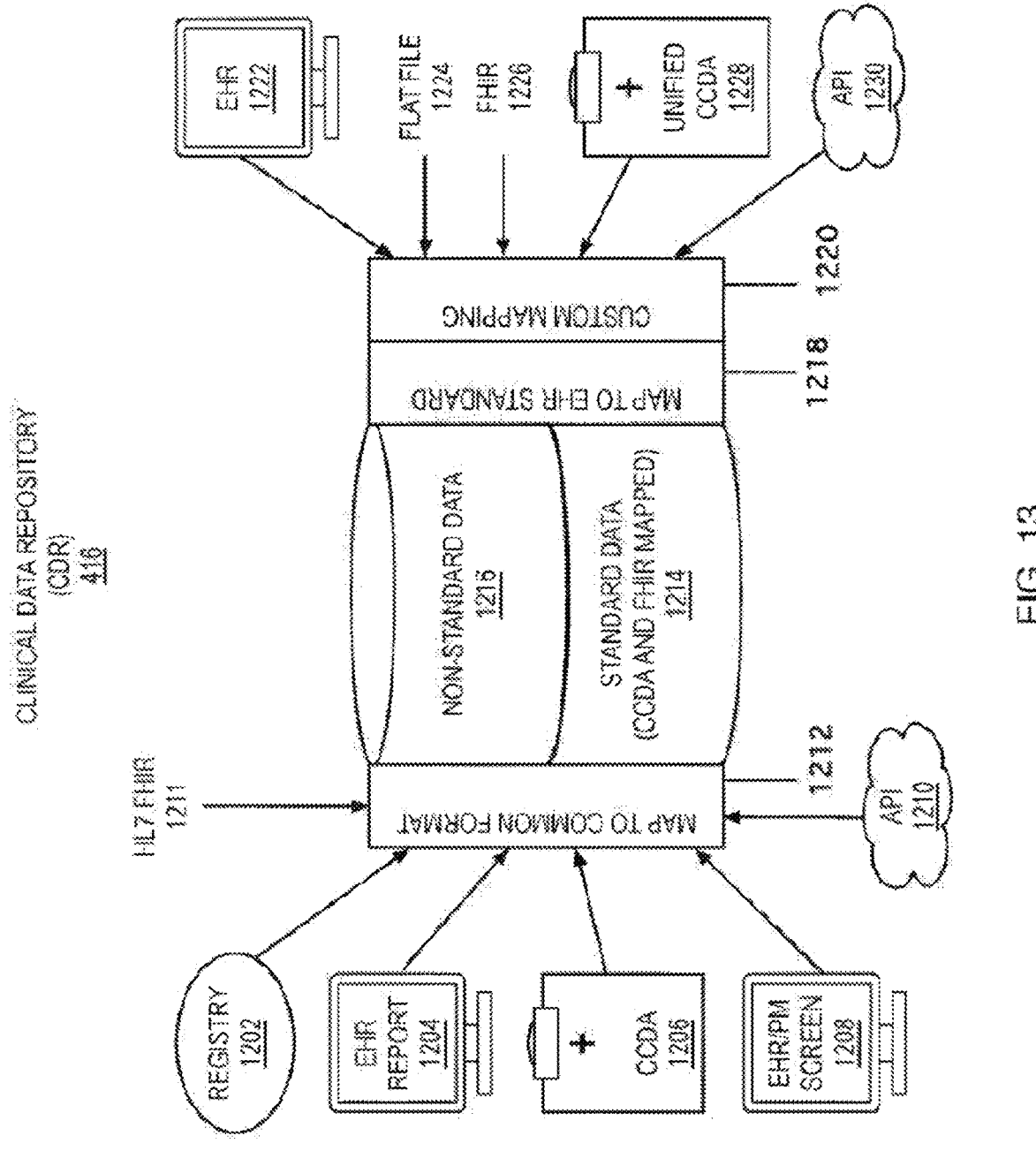
FIG. 13

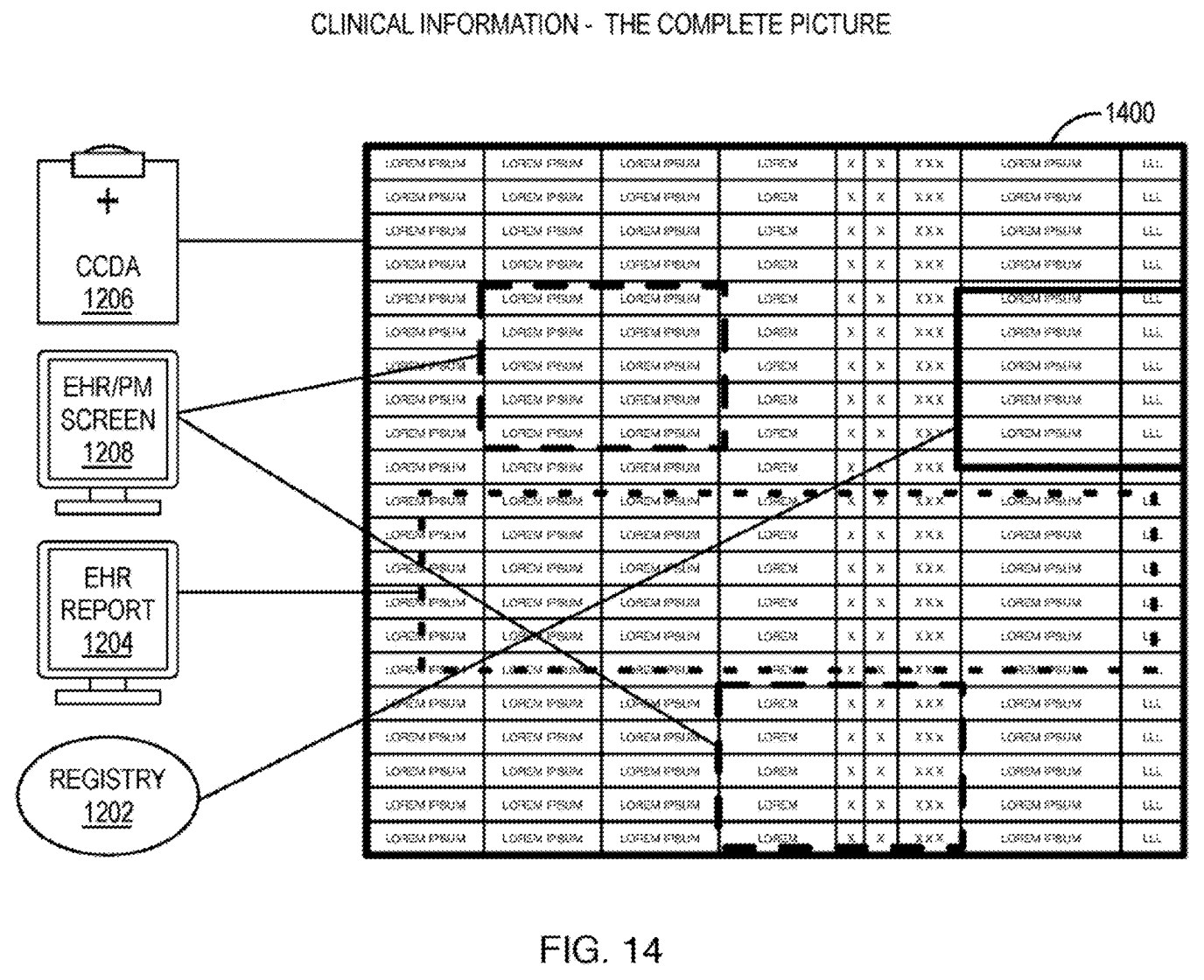

CLINICAL INFORMATION - THE COMPLETE PICTURE

FIG. 14

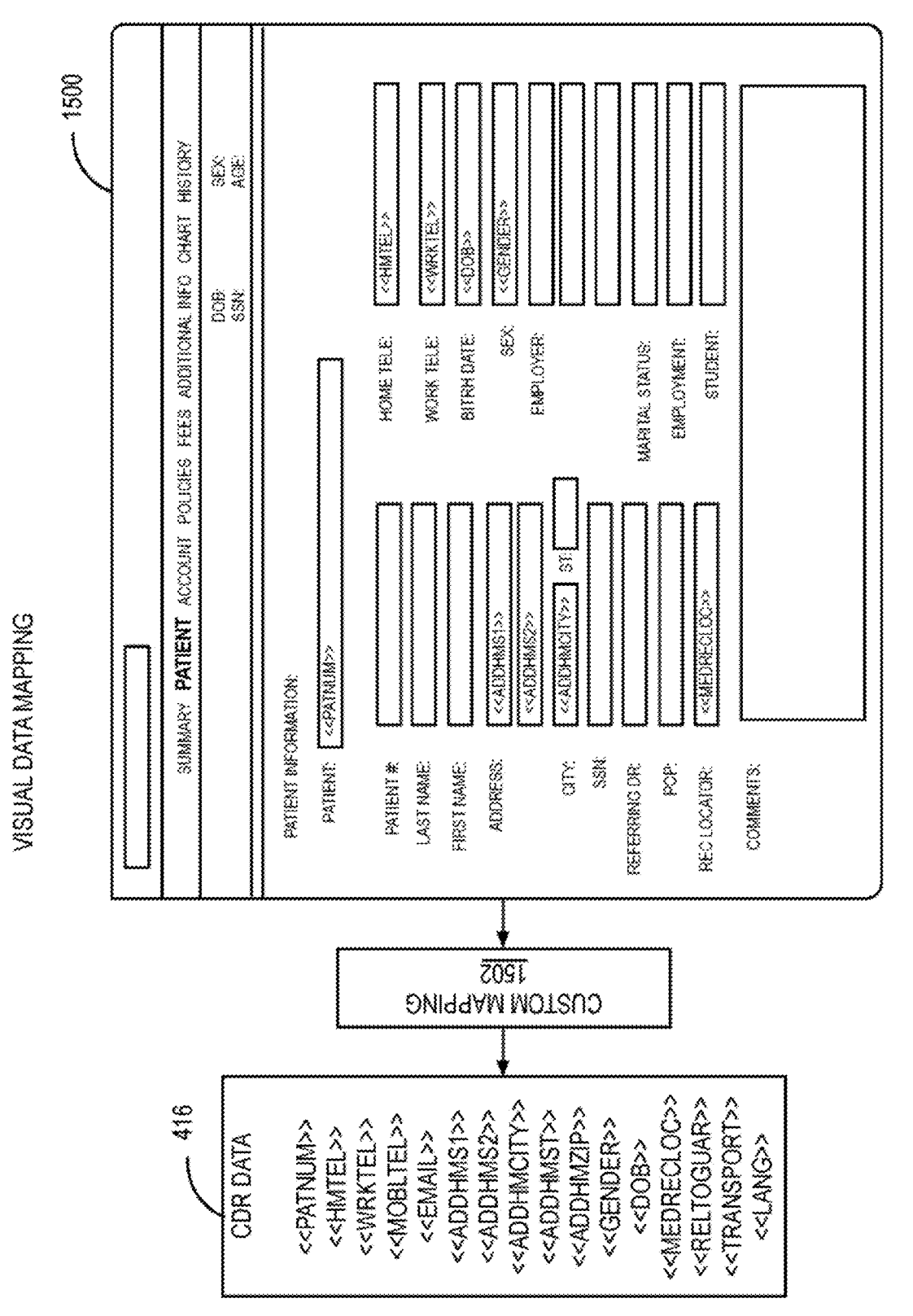
FIG. 15

FIG. 16

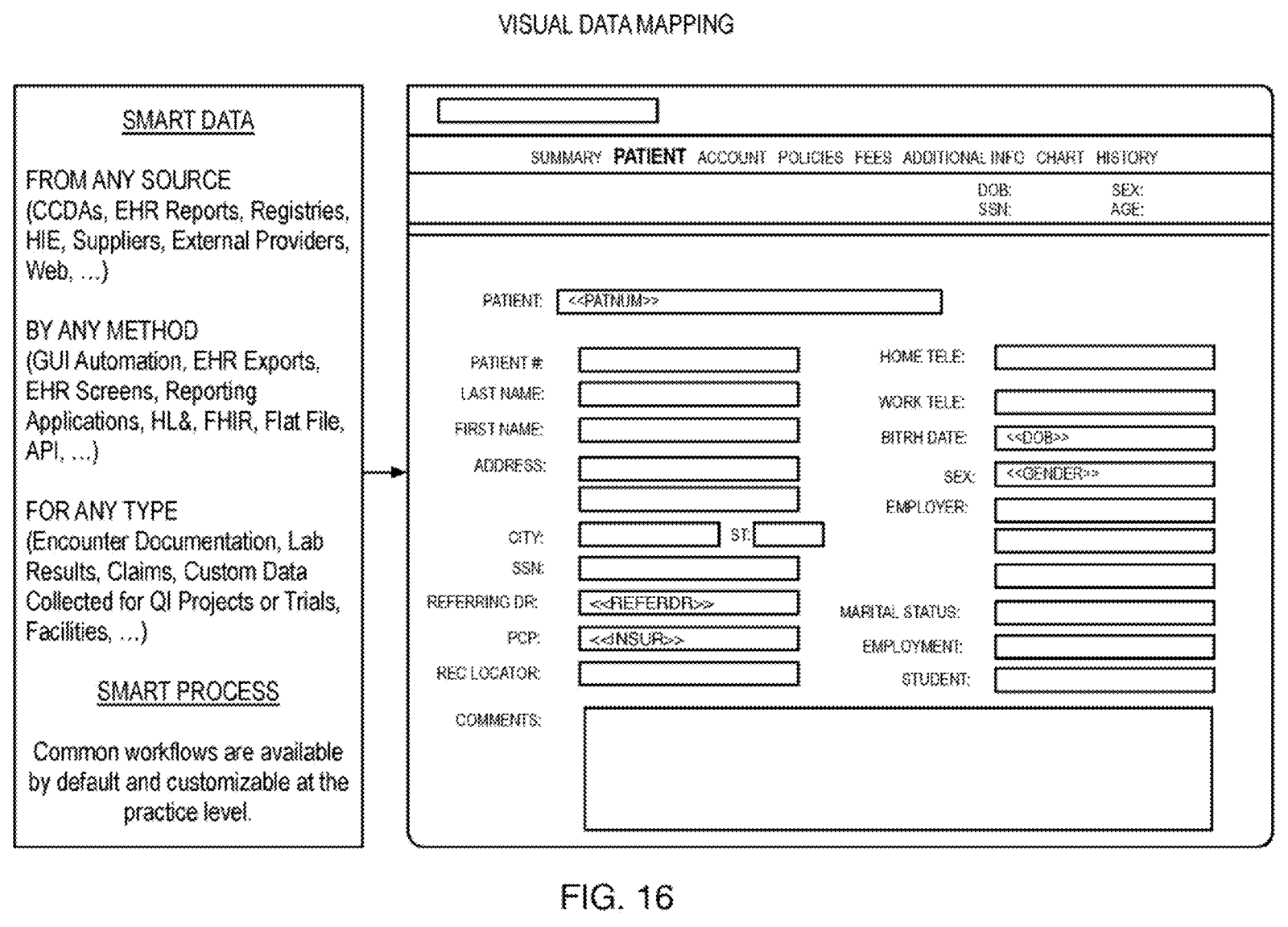

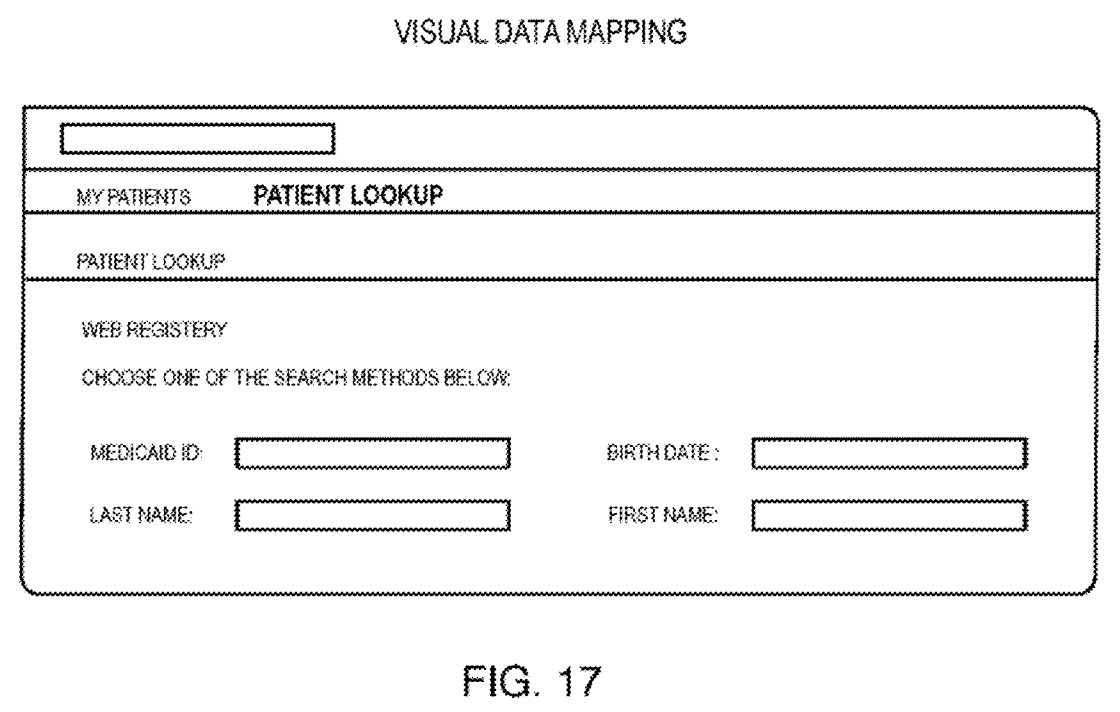

VISUAL DATA MAPPING

MY PATIENTS     PATIENT LOOKUP

PATIENT LOOKUP

WEB REGISTERY

CHOOSE ONE OF THE SEARCH METHODS BELOW:

MEDICAID ID:

LAST NAME:

BIRTH DATE:

FIRST NAME:

FIG. 17

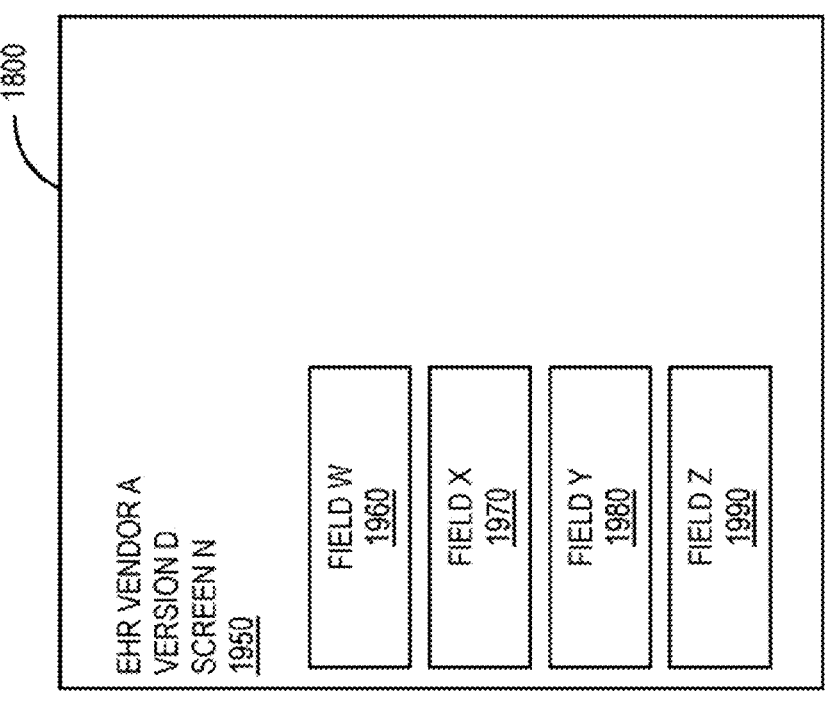
1800
EHR VENDOR A
VERSION D
SCREEN N
1950
FIELD W
1960
FIELD X
1970
FIELD Y
1980
FIELD Z
1990
FIG. 19
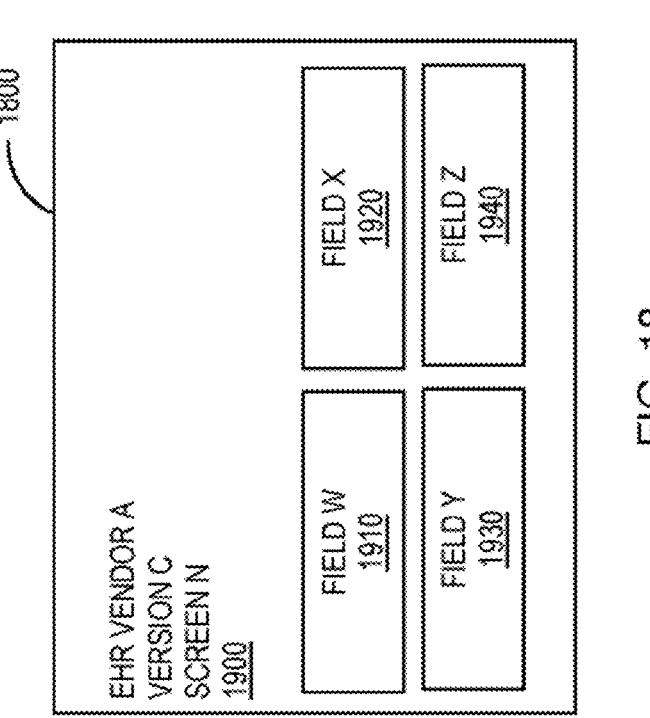
1800
EHR VENDOR A
VERSION C
SCREEN N
1900
FIELD W
1910
FIELD X
1920
FIELD Y
1930
FIELD Z
1940
FIG. 18

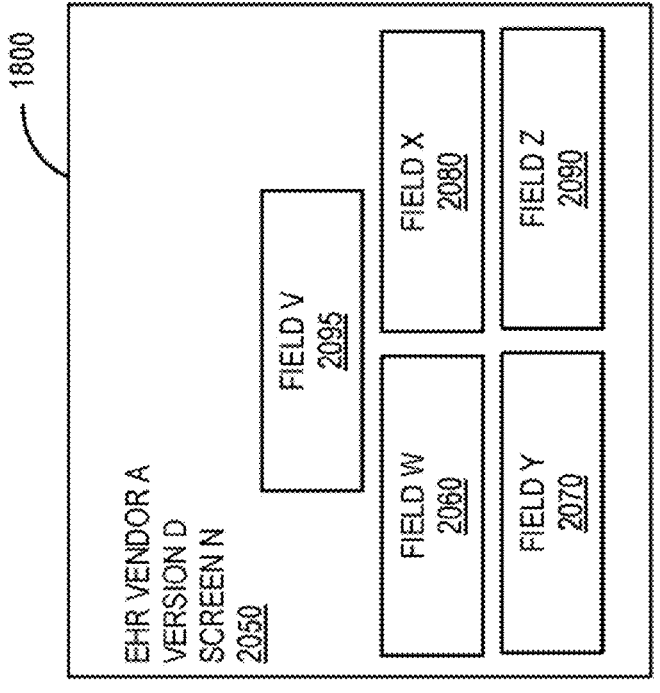
FIG. 20B
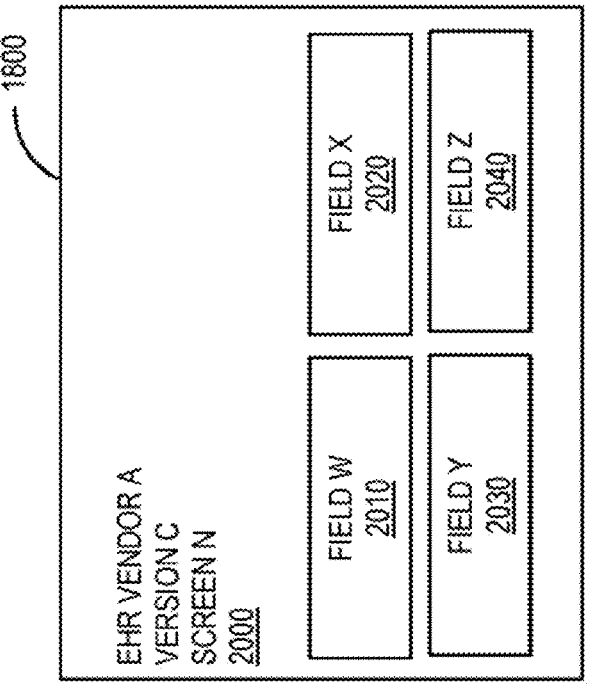
FIG. 20A

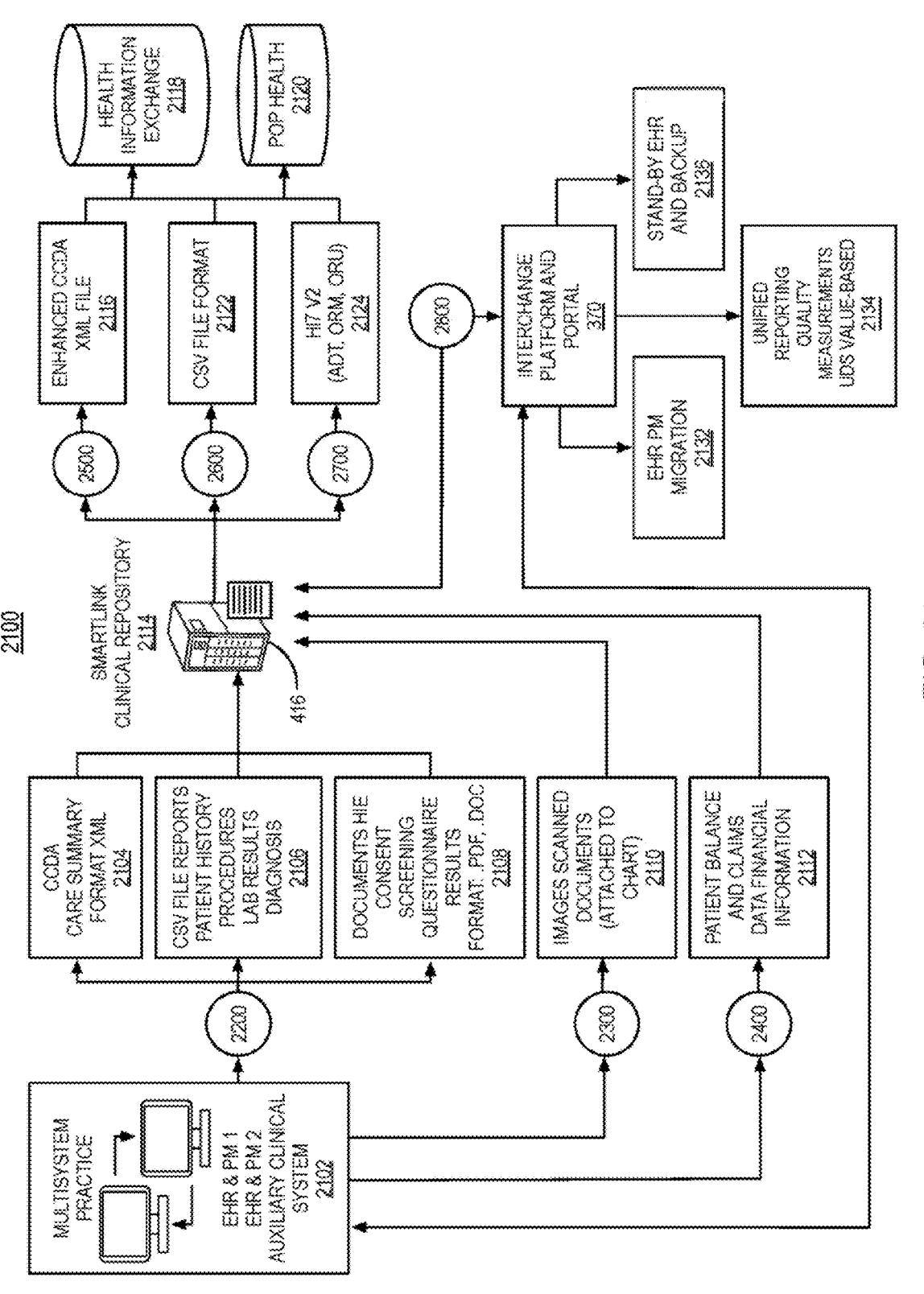
FIG. 21

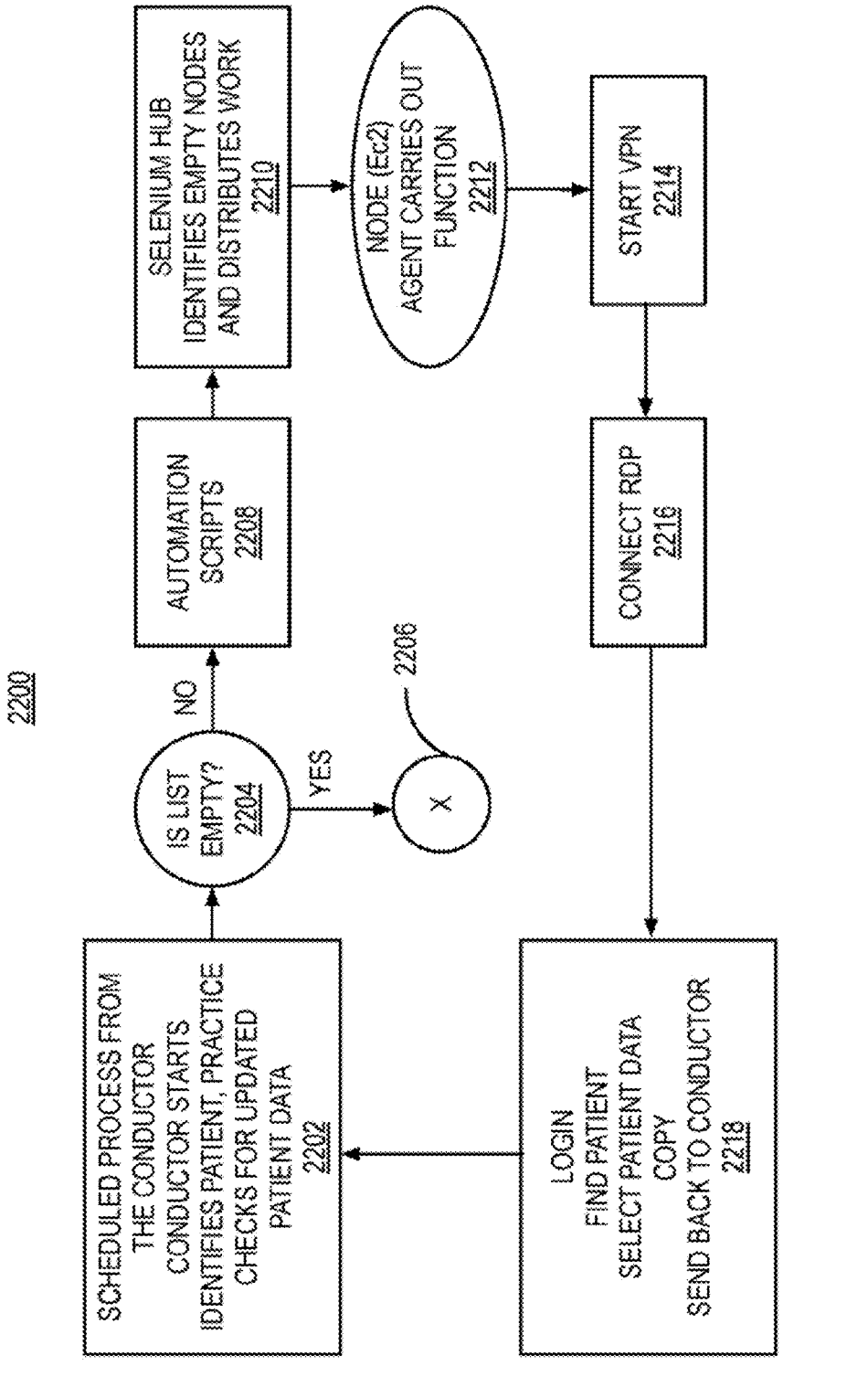
FIG. 22

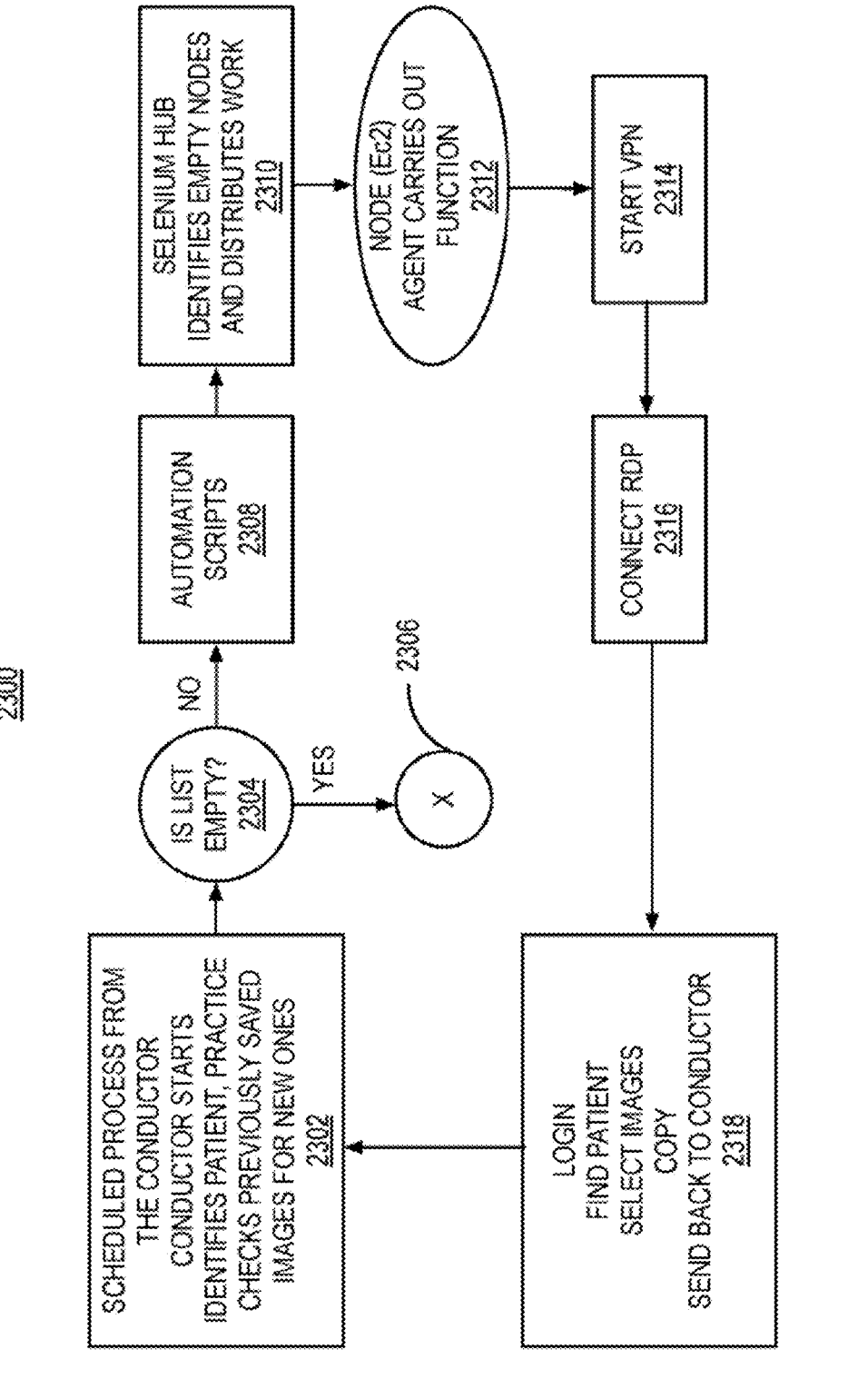
FIG. 23

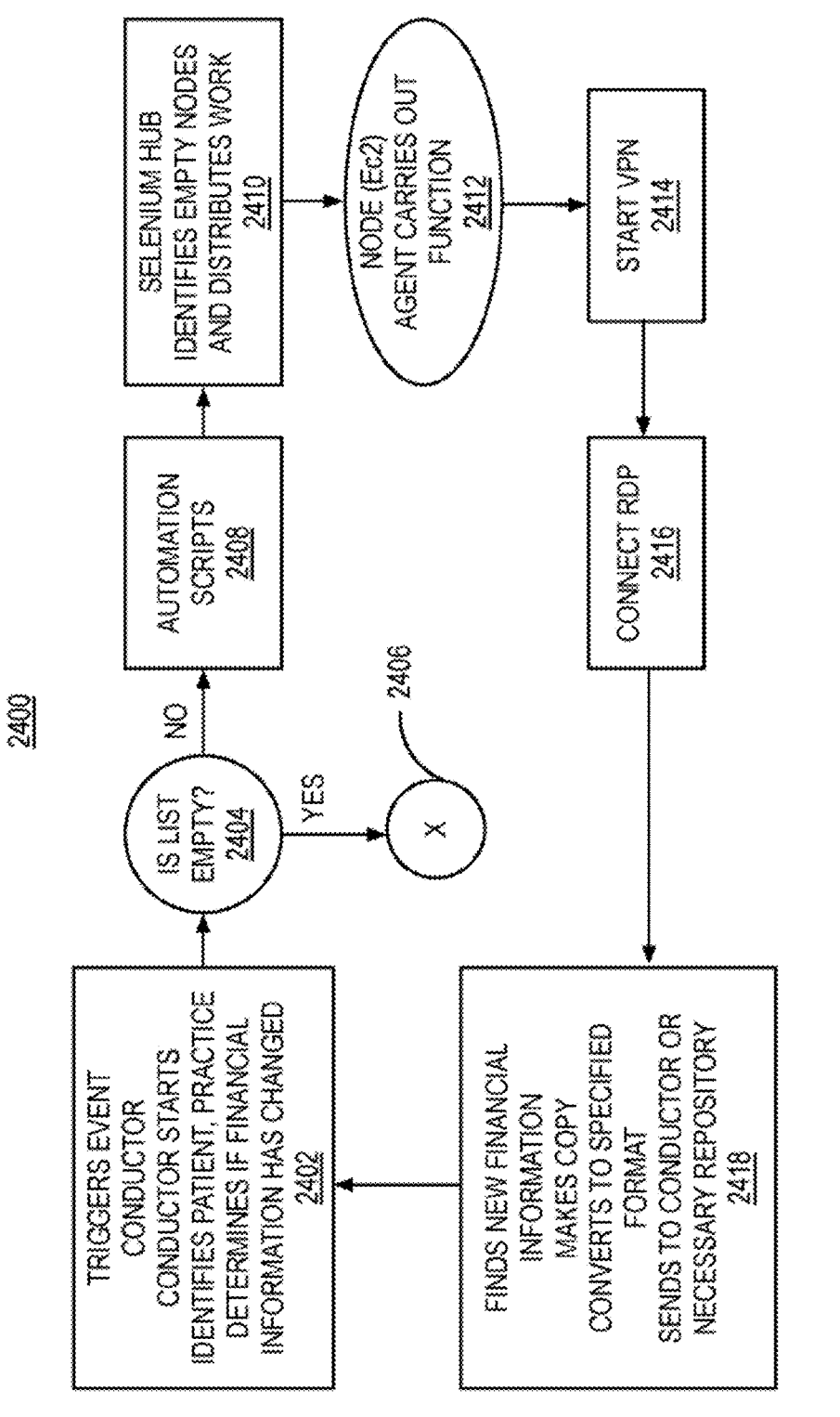
FIG. 24

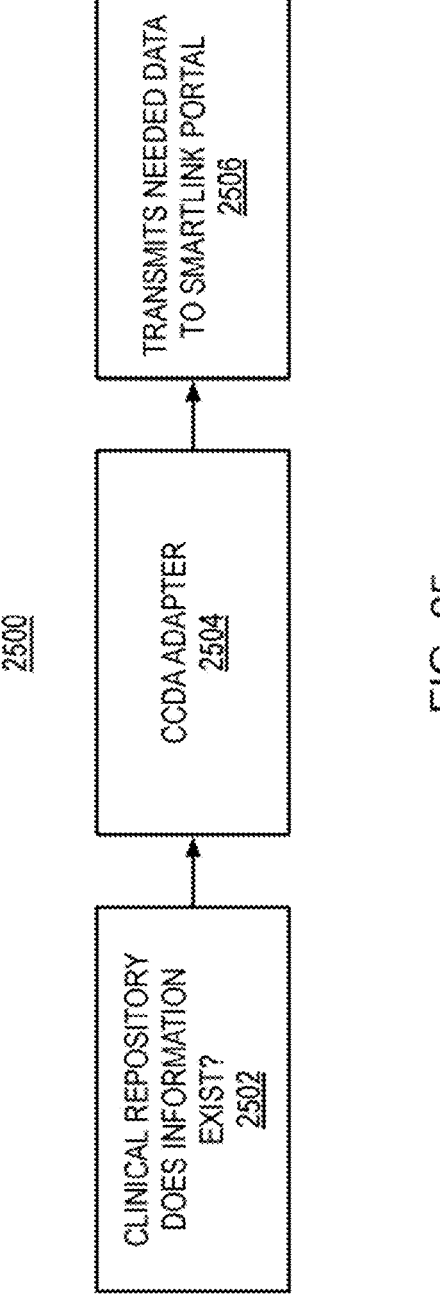
FIG. 25

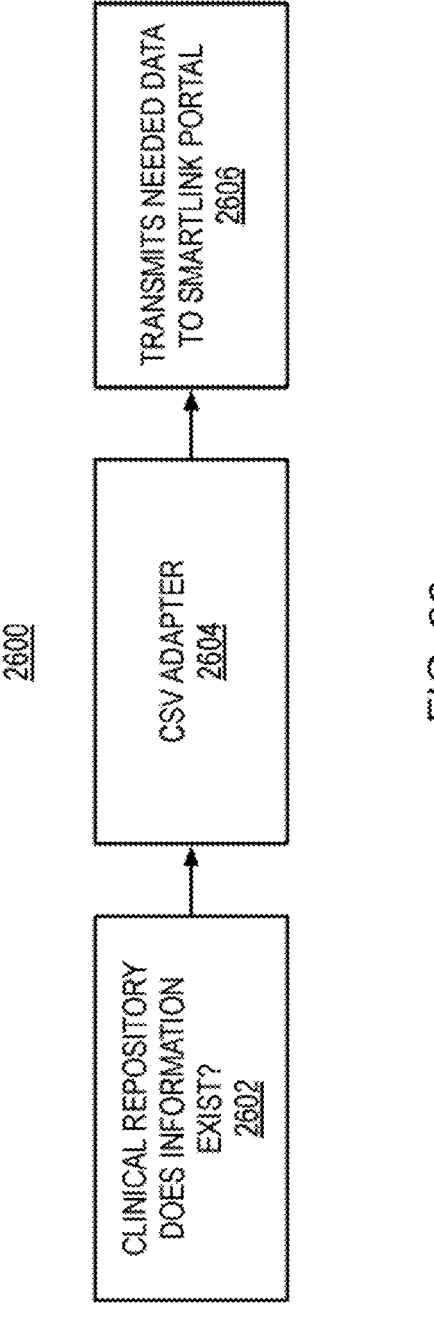
FIG. 26

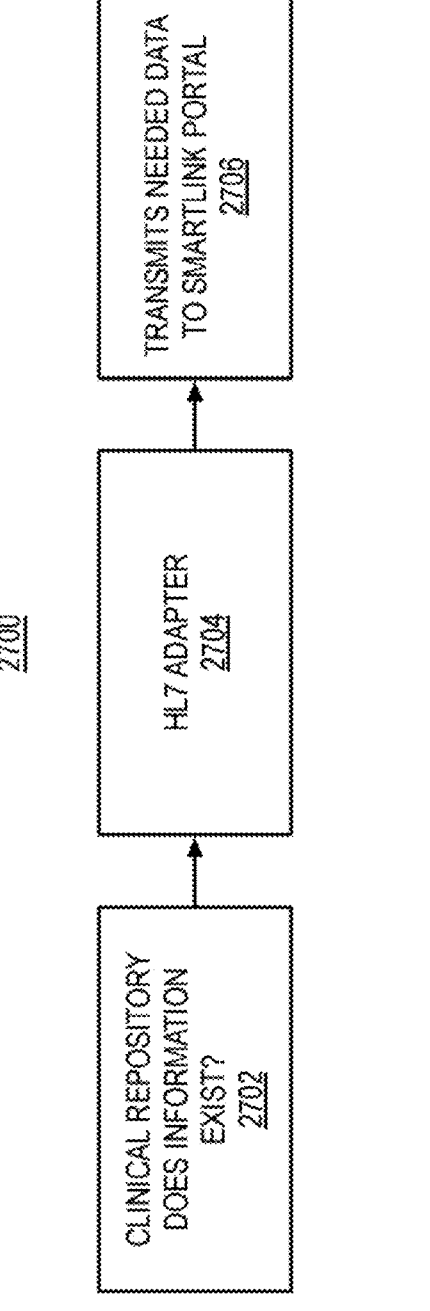
FIG. 27

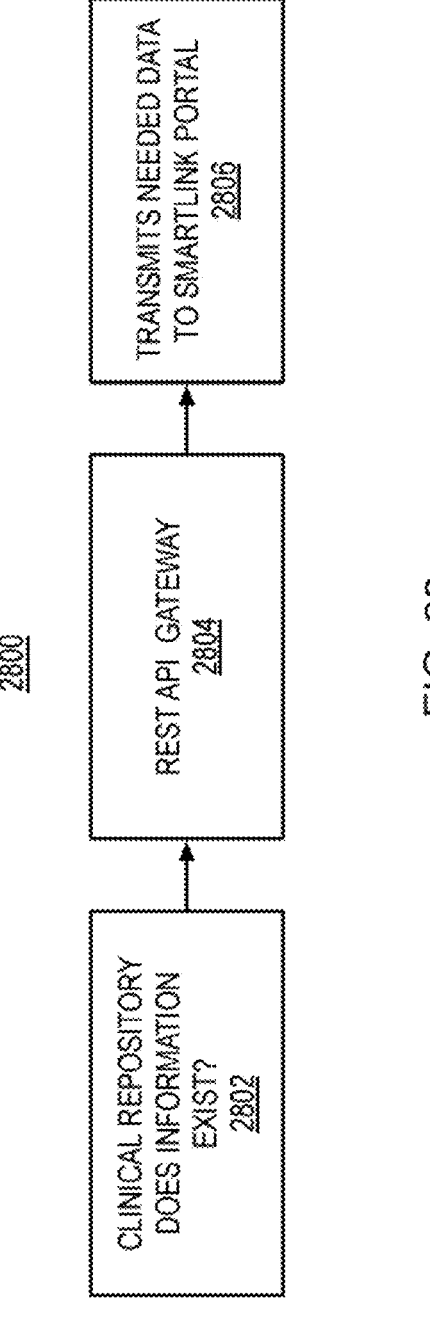
FIG. 28

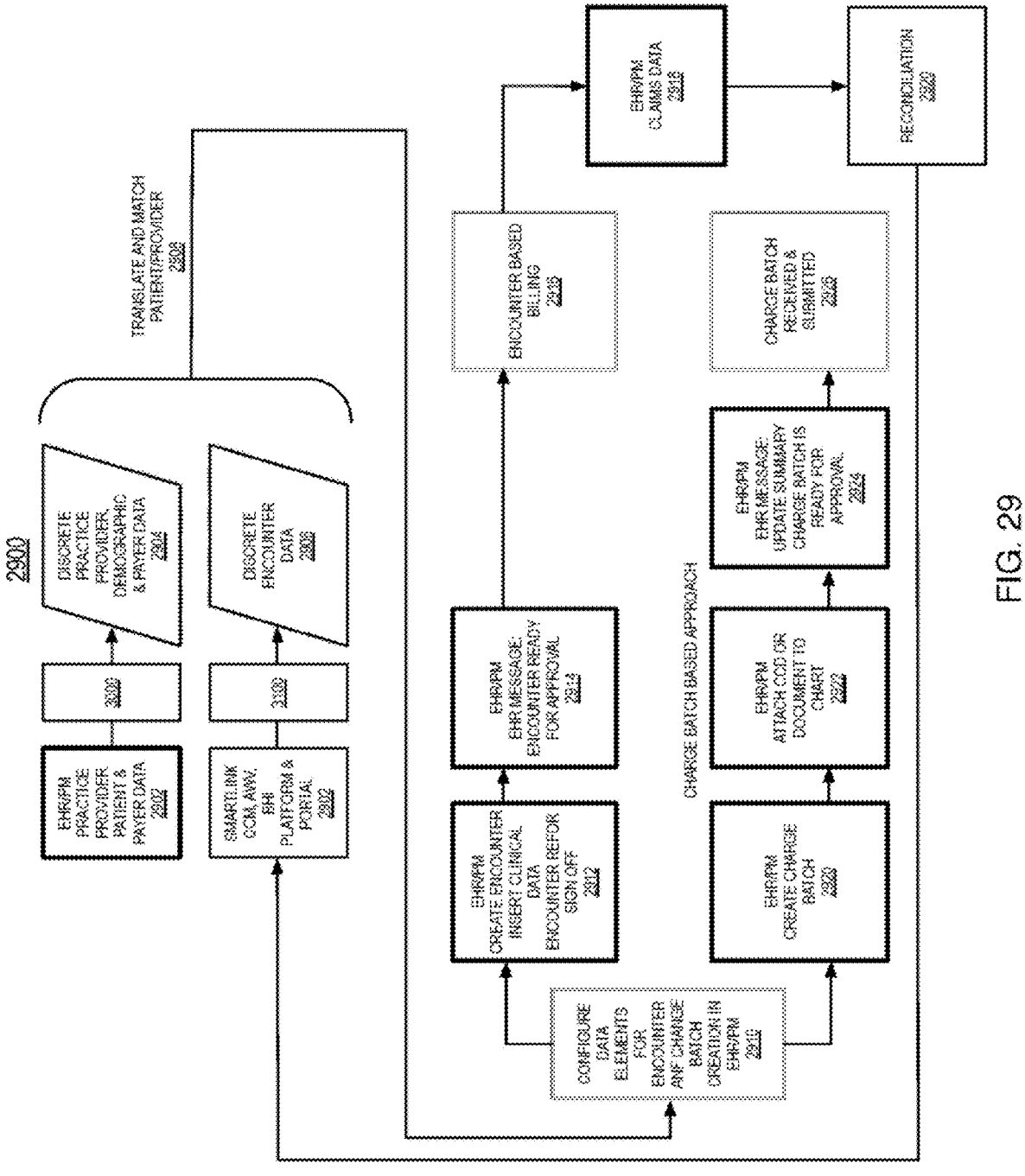
FIG. 29

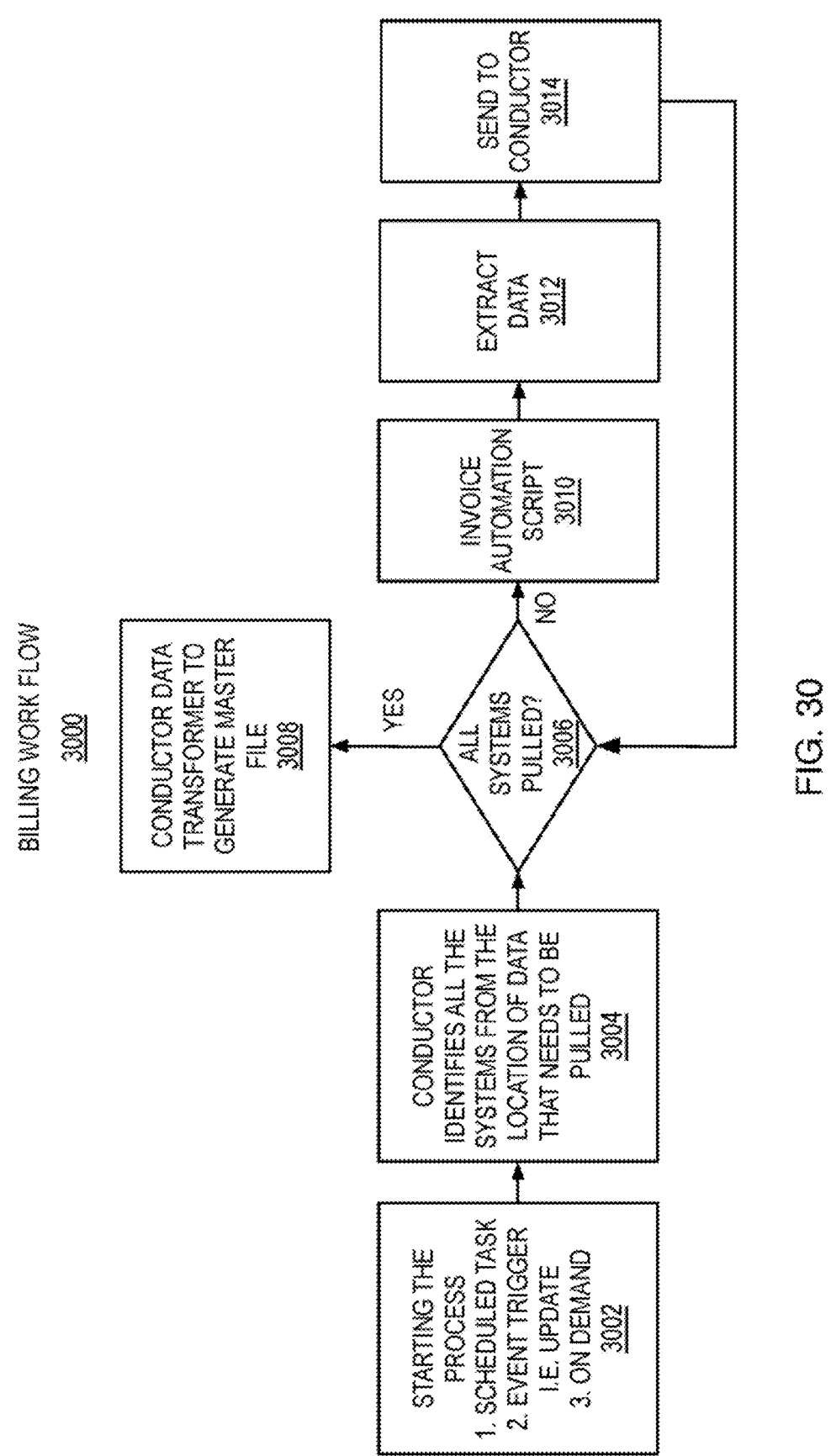
FIG. 30

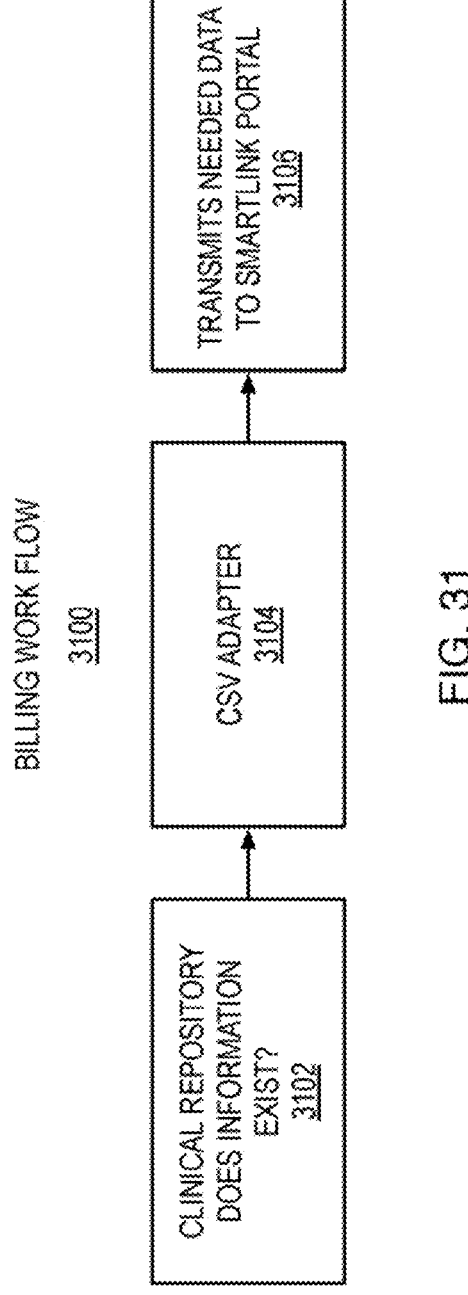
FIG. 31

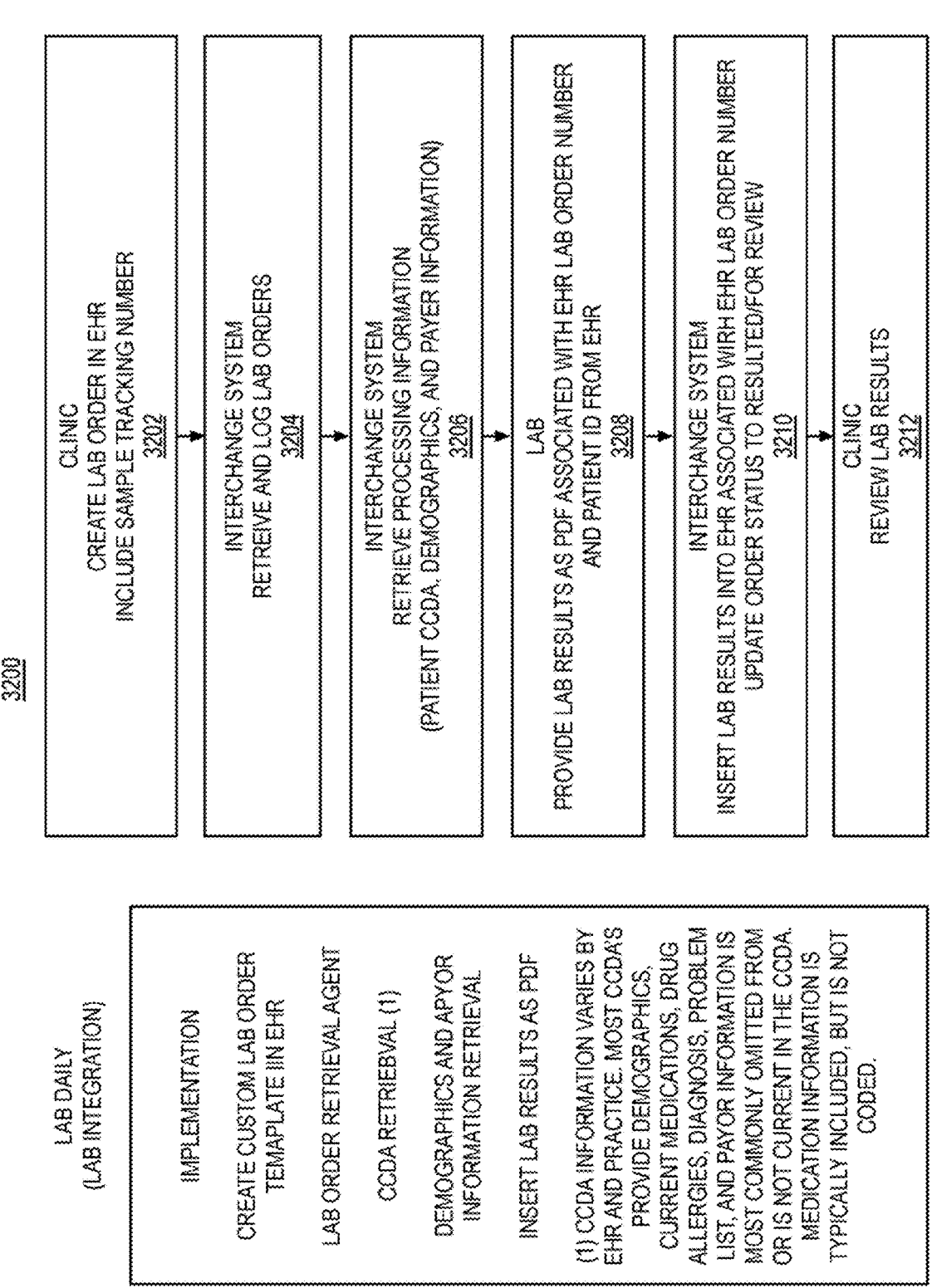
FIG. 32

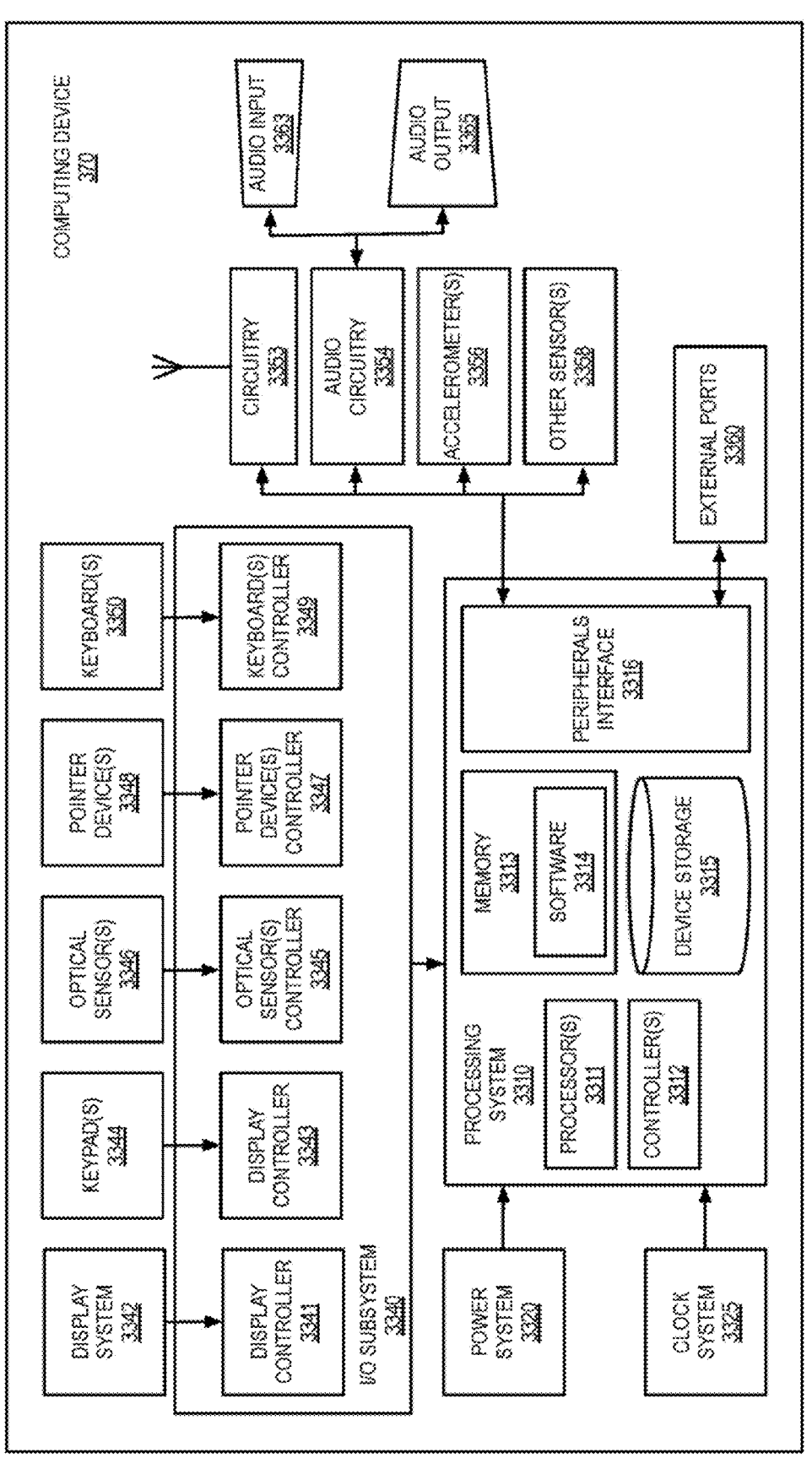
FIG. 33

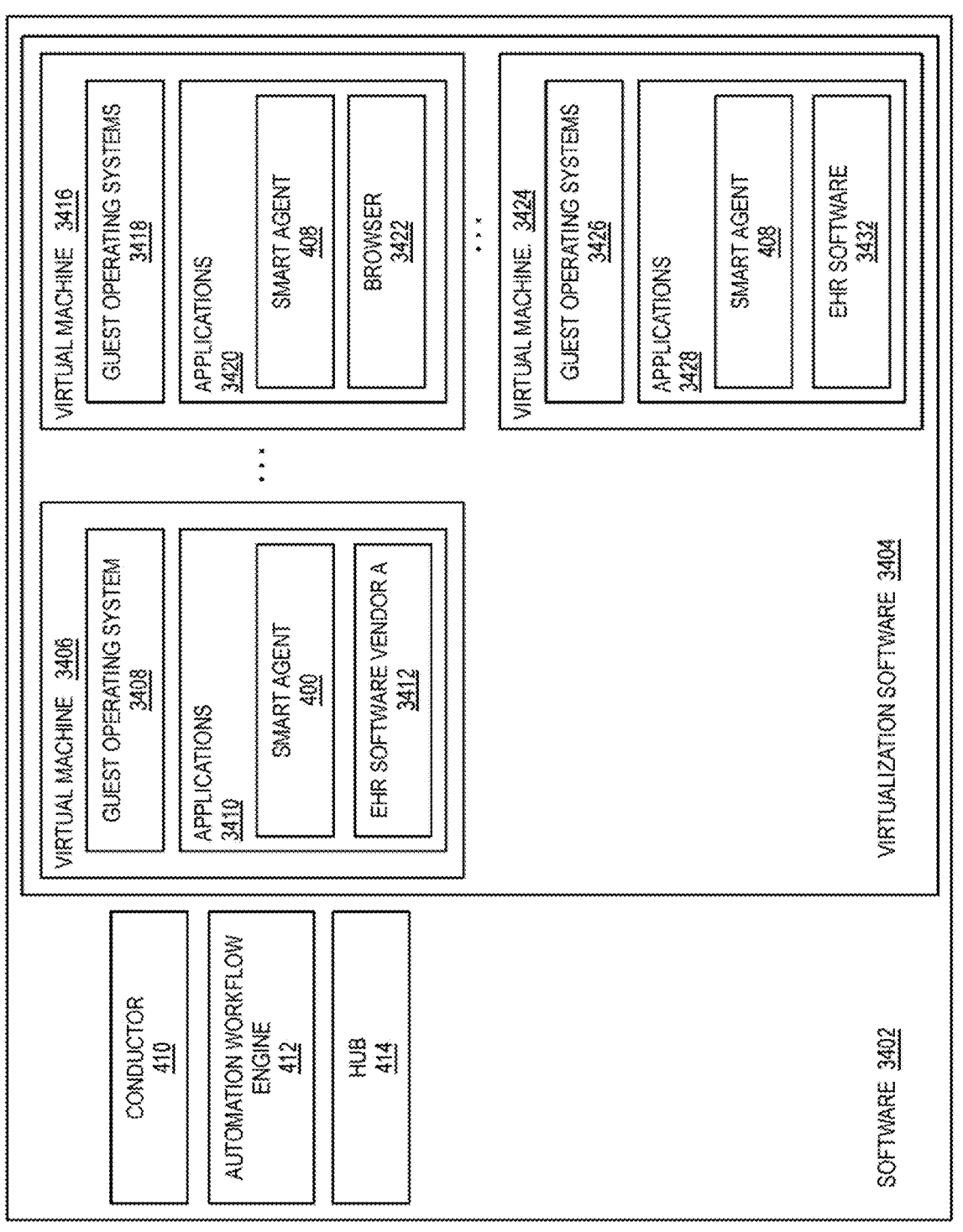
FIG. 34

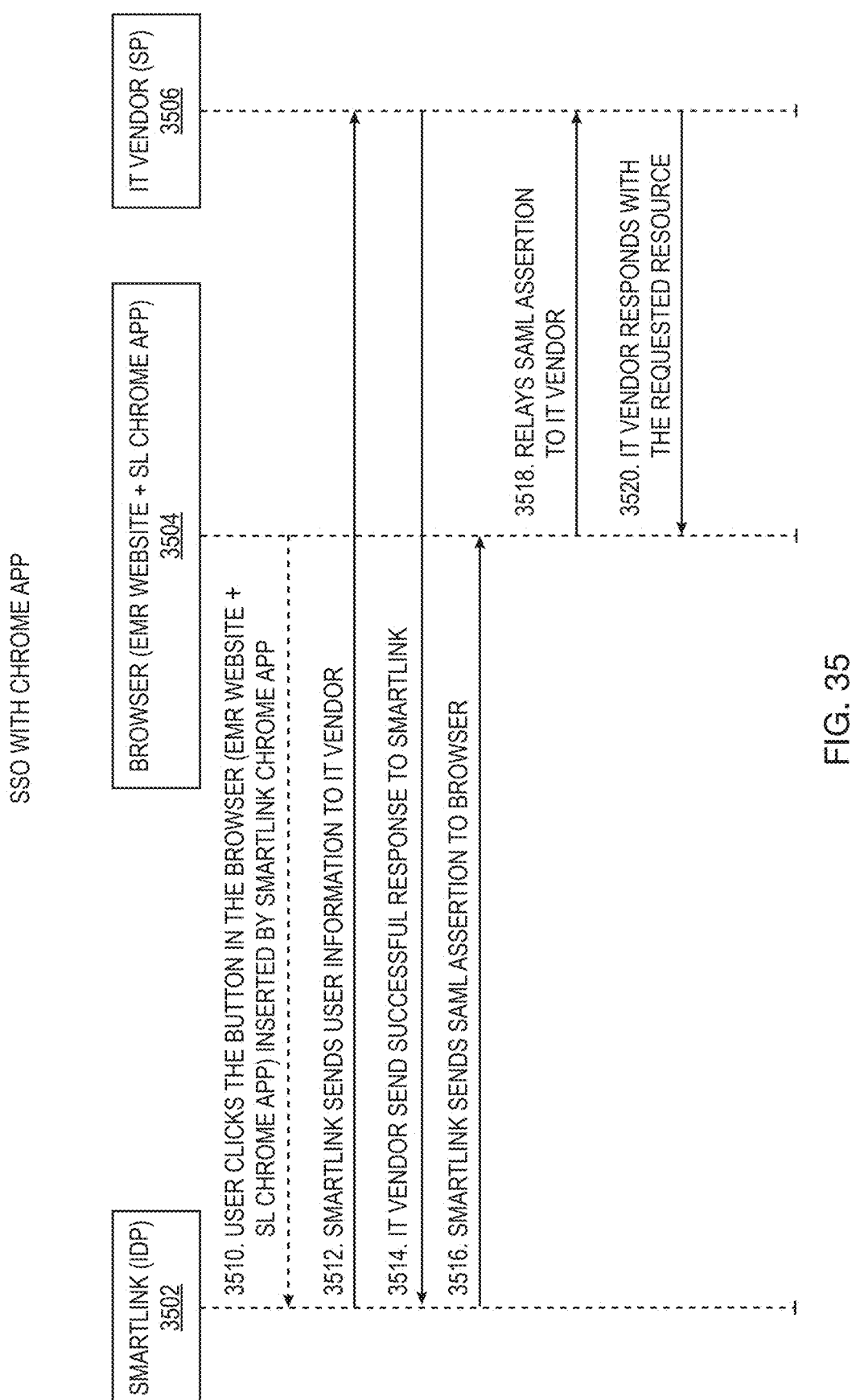

SSO WITH CHROME APP

3500

SMARTLINK (IDP) 3502

BROWSER (EMR WEBSITE + SL CHROME APP) 3504

IT VENDOR (SP) 3506

3510. USER CLICKS THE BUTTON IN THE BROWSER (EMR WEBSITE + SL CHROME APP) INSERTED BY SMARTLINK CHROME APP

3512. SMARTLINK SENDS USER INFORMATION TO IT VENDOR

3514. IT VENDOR SEND SUCCESSFUL RESPONSE TO SMARTLINK

3516. SMARTLINK SENDS SAML ASSERTION TO BROWSER

3518. RELAYS SAML ASSERTION TO IT VENDOR

3520. IT VENDOR RESPONDS WITH THE REQUESTED RESOURCE

FIG. 35

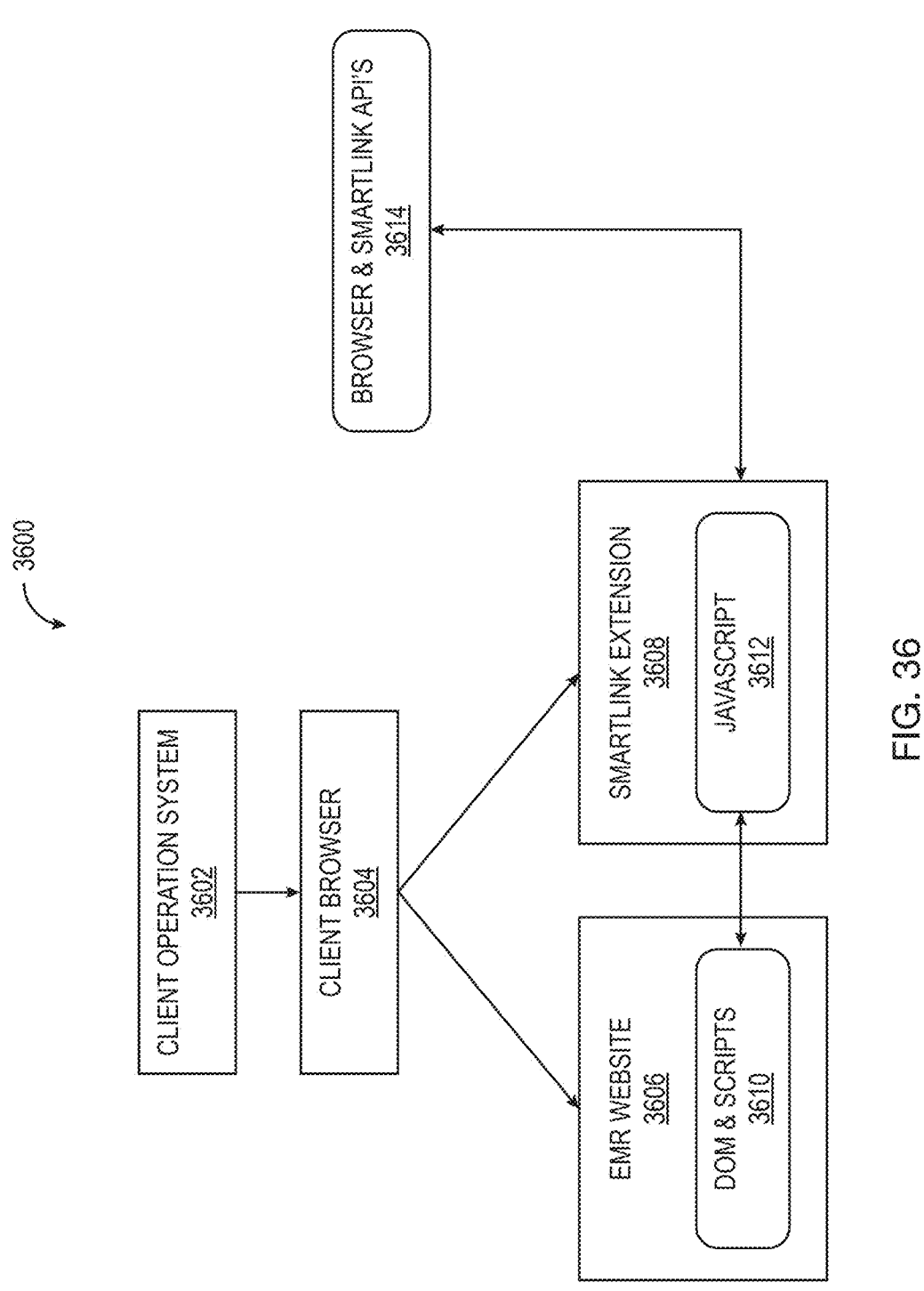
FIG. 36

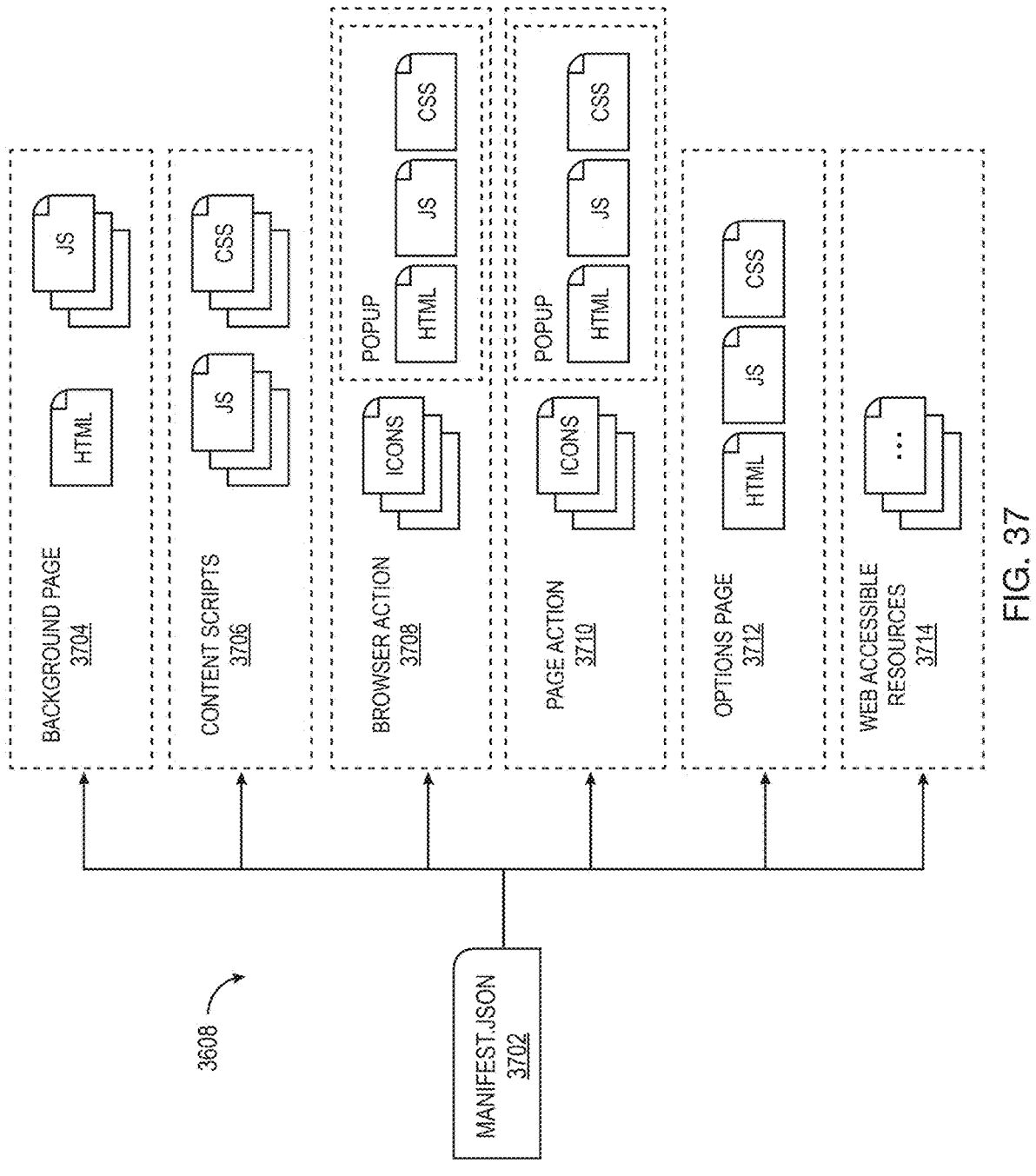
FIG. 37

EXTENSION OF USER INTERFACE BASED SOFTWARE INTEGRATION TO NEAR REAL TIME AND SINGLE SIGN ON

CROSS-REFERENCE TO RELATED APPLICATIONS

This application claims the benefit of U.S. patent application Ser. No. 16/661,661 filed on Oct. 23, 2019; which claims priority to U.S. Provisional Patent Application Ser. No. 62/749,817, filed Oct. 24, 2018; both of which are incorporated herein by reference.

FIELD OF THE DISCLOSURE

The present disclosure relates to the interchange of data in and between clinically integrated networks (CINs).

BACKGROUND OF THE DISCLOSURE

The U.S. healthcare system has traditionally been a fee-for-service model that focuses on the number of healthcare services provided, often without regard to patient outcomes. This model has been criticized for contributing to the runaway cost of healthcare in the U.S. where healthcare expenditures topped $4.3 trillion or 18.3% of the U.S. gross domestic product (GDP) in 2021 versus 5% of U.S. GDP in 1960. Through Medicaid programs for the economically disadvantaged and Medicare programs for the elderly, the U.S. government is one of the largest purchasers of health-care services in the nation. In an effort to control rising costs for those programs, the U.S. government is fostering a value based care (VBC) model for healthcare that focuses on lowering the cost of care across providers and better overall patient outcomes.

SUMMARY

Aspects of the current disclosure include a system of updating electronic health records (EHRs) comprising: a conductor capable of receiving a triggering event, creating a package made up of a sequence of automation scripts and sending a data extraction request to an automation workflow engine; the automation workflow engine capable of adding to the package artifacts that are needed to execute an automation workflow made up of the automation scripts and forwarding the package to a hub; the hub configured to determine based on the package at least one node of a plurality of nodes associated with a plurality of EHR clients for executing the automation workflow and then forwarding the package to the at least one node; and the at least one node capable of executing the automation workflow including sending commands to the associated EHR client and extracting targeted medical data.

Further aspects of the disclosure include a method of updating electronic health records (EHRs) comprising: receiving a triggering event at a conductor located on a server; creating a package made up of a sequence of automation scripts and sending a data extraction request to an automation workflow engine; adding to the package at the automation workflow engine artifacts that are needed to execute an automation workflow made up of the automation scripts; forwarding the package to a hub; determining at the hub based on the package at least one node of a plurality of nodes associated with a plurality of EHR clients for executing the automation workflow and then forwarding the package to the at least one node; and executing at the at least one node the automation workflow including sending commands to the associated EHR client and extracting targeted medical data.

Further aspects of the disclosure include a method of updating electronic health records (EHRs) comprising: receiving a triggering event at a conductor located on a server; creating a package made up of a sequence of automation scripts and sending a data extraction request to an automation workflow engine; adding to the package at the automation workflow engine artifacts that are needed to execute an automation workflow made up of the automation scripts; forwarding the package to a hub; determining at the hub based on the package a plurality of nodes associated with a plurality of EHR clients for executing the automation workflow and then forwarding the package to the plurality of nodes; executing at the plurality of nodes the automation workflow including sending commands to a plurality of EHR clients and extracting targeted medical data; and concatenating the targeted medical data from the plurality of EHR clients.

BRIEF DESCRIPTION OF THE DRAWINGS

FIG. 1 illustrates a prior art Clinically Integrated Network (CIN) with different Electronic Health Record (EHR) systems from different vendors.

FIG. 2A-D illustrate existing expensive, complex, and time consuming options for interchange of data in CINs.

FIG. 3 illustrates an improved interchange system and method over that of the prior art FIG. 1.

FIG. 4 shows a "front-end" approach for the interchange system and method 370 that emulates a user's access to EHR.

FIG. 5 shows a high level flow of the interchange system and method 370.

FIG. 6 illustrates the configuration details about a node accessing an EHR system that is on premises.

FIG. 7 illustrates the configuration details about a node accessing a cloud based EHR.

FIG. 8 illustrates an automation workflow in the interchange system and method 370.

FIG. 9 illustrates the structure maintained in the repository 416.

FIG. 10 shows how the smart agent 408 and the conductor 410 coordinate.

FIG. 11 shows the error handling between the smart agent 408 and an exemplary auditing and quality node.

FIG. 12 shows the Clinical Data Repository (CDR) (or Clinical Data Warehouse (CDW)) 416 of the interchange system and method 370 and the types of reports that can be generated from the data stored in the repository 416.

FIG. 13 is similar to FIG. 12 except in FIG. 12 it is shown how the raw data delivery types are supported.

FIG. 14 shows the inputs into the interchange system including CDR—CCDA, EHR/PM Screen, EHR Report, or Registry.

FIG. 15 shows visual data mapping and illustrates how data is pulled out of the interchange system repository 416 and formatted for delivery to a client EHR.

FIG. 16 is an illustration of how the interchange system and method 370 makes common workflows available to medical practices by default for common data elements, but practices can customize their own workflows for additional data not covered, simply by clicking the desired field and drag and drop.

FIG. 17 illustrates that the interchange system and method 370 can enter and extract information in the same workflow.

FIGS. 18 and 19 illustrate how a screen may change for a particular EHR vendor between versions, but by using automated testing tools, as long as the field names are retained, the workflow automation scripts will continue to work fine.

FIGS. 20A-20B illustrate how a screen may change for a particular EHR vendor between versions and new field elements are added. And how the interchange system 370 can detect the change and fix it once for all EHR vendors who have migrated asynchronously to that new version.

FIG. 21 illustrates an exemplary work flow for a multi-system organization similar to one shown in FIG. 3.

FIG. 22 illustrates process 2200 which is a scheduled update of select patient information illustrating coordination of the conductor 410 and smart agent 408.

FIG. 23 shows a process 2300 which is a scheduled update of select images illustrating coordination of the conductor 410 and smart agent 408 with the ability to retrieve non-discrete data.

FIG. 24 shows a process 2400 is the triggered update of financial or payer data associated with a patient.

FIG. 25 details step 2500 in FIG. 21.

FIG. 26 details step 2600 in FIG. 21.

FIG. 27 details step 2700 in FIG. 21.

FIG. 28 details step 2800 in FIG. 21.

FIG. 29 shows one type of work flow 2900 for a billing integration for a CIN 300 such as the one shown in FIG. 3.

FIG. 30 references block 3000 in FIG. 29.

FIG. 31 references block 3100 in FIG. 29.

FIG. 32 shows how the conductor 410 and smart agent 408 coordinate specific data such as clinical orders bi-directionally with a third party vendor such as a laboratory.

FIG. 33 shows the basic hardware elements of a general computing device (server, PC, phone, tablet).

FIG. 34 shows the basic elements of a virtual machine used in the interchanged system and method 370 described herein.

FIG. 35 shows the sequence diagram for single sign-on using a browser application, such as a Chrome app, according to embodiments of the present disclosure.

FIG. 36 shows the architecture diagram of the browser application according to embodiments of the present disclosure.

FIG. 37 provides more detail on the architecture of the browser application according to embodiments of the present disclosure.

DETAILED DESCRIPTION OF THE DISCLOSURE

Many insurers are increasingly adopting value based care (VBC) models. One aspect of this approach for the government originated with the American Recovery and Reinvestment Act of 2009 (ARRA). The ARRA included stimulus expenditures for the development and adoption of healthcare information technology (HIT) for the health care industry. One of the largest allocations of funding included incentive payments in Medicare and Medicaid reimbursement systems for healthcare providers who became meaningful users of certified electronic health records (EHR) technology. The law required providers to demonstrate a meaningful use (MU) of EHR by 2015 or they would not receive incentive payments and their reimbursement payments under Medicare would be reduced. To demonstrate meaningful use of certified EHR technology, the provider had to achieve different measures across three stages. At a high level, Stage 1 involved the adoption of EHR technology and data gathering. Stage 2 emphasized interchange of patient information and care coordination. Stage 3 focused on improving healthcare outcomes.

Two challenges have emerged with respect to VBC which align with Meaningful Use Stage 2 ("MU2"). The first challenge involves the exchange of patient information. Traditional EHR technology was initially configured with the goal of keeping sensitive health information protected and secure. It was not configured with the perspective that it would be necessary to collaborate with other healthcare providers. With healthcare payment models under transformation and an emphasis on paying for performance rather than services, a provider's ability to collaborate and electronically share information is increasingly becoming a requirement for treating patients and getting reimbursements. To assist in the collaboration and sharing of information, the Office of the National Coordinator (ONC) for HIT required healthcare providers to use the Health Level 7 (HL7) Consolidated Clinical Document Architecture (C-CDA) in order to meet the certifications of Meaningful Use Stage 2. HL7 C-CDA defines both a document standard (a format for clinical documents that is both human readable and machine processable) and a messaging standard (a format for clinical documents that is only machine processable). The ONC further created the Direct Messaging project, which is a scaled down version of the Nationwide Health Information Network (NwHIN) that permits the secure direct interchange of messages containing medical health records, typically manually invoked one message at a time. Direct Messaging can be thought of as secure email for the healthcare industry. It is also possible to interchange the C-CDA information through integrations with each EHR (often involving different interfaces and protocols). The second challenge with respect to VBC involves the collaboration itself. The collaboration of vendors with respect to pricing and outcomes is typically the type of behavior which would violate various federal and state antitrust regulations configured to promote fair competition in business for the benefit of consumers. In the U.S., exemptions have been made to antitrust laws to permit healthcare providers to collaborate provided that they are able to integrate patient data and negotiate pricing with those paying for the healthcare services (usually the Federal Government or large insurers).

Healthcare data is complex due to many different elements and time history which is required. As discussed above, software that captures patient medical history is called EHR or EMR (Electronic Medical Record(s)). Two typical methods for capturing patient medical history include: HL7 interface purchased via EHR vendors (or a third partner vendor like Merge™) and direct access to an EHR database. Direct access only works for "on-premise" EHR and not "cloud based" EHR. It also cannot write back to an EHR since it would void most vendor support contracts and usage agreements.

The transformation to VBC has led many healthcare providers to create an umbrella organization, often referred to as a Clinically Integrated Network (CIN), that involves multiple healthcare providers and clinics in different locations with different specialties oftentimes with different EHR technology all working to lower the overall cost of patient care while increasing the quality and improving outcomes of healthcare treatment. To achieve the goal of a CIN to lower total medical cost and/or improve outcomes, the CIN must collect, normalize, and update clinical information for all or nearly all patients within the network into a centralized location. Patient records must be updated when new data is available from each healthcare provider in the network such as a hospitalization, specialist visit, or a new encounter at the primary care clinic. Traditional CIN integrations typically cost from $5,000-$50,000 per clinic for the initial integration and have significant ongoing support cost to maintain and repair the integrations. Most practices require several integrations for services such labs, health information interchange (HIE), hospital systems, and referral providers. As will be discussed in connection with FIG. 2A even for a simple CIN with for example, seven providers, there are many permutations for conversions among systems. The traditional approach to clinical integration requires highly skilled software developers and data architects to integrate one system with another, often taking a month or more to complete one clinic. With over 500 EHR vendors in the US alone the task of integrating diverse EHR technology becomes prohibitively expensive and time consuming. The party responsible for the CIN's overall integration then has to connect all of its provider's disparate EHR interfaces and maintain their connections to a centralized location, a task that could cost tens of millions of dollars for the initial integration and a significant amount to maintain it. Often to control cost, the integrations are minimal, in that information may only flow in one direction and only specific defined data elements may be available through the application programing interface. The traditional approach to systems integration simply does not easily scale down to a typical physician's office, nor do they provide sufficient agility to satisfy specific clinical information needs required to effectively deliver VBC. In reality, these practices simply cannot bear the financial burden of traditional systems integration and have either opted not to participate or use manual processes.

Therefore, there is a need for an interchange system, method, and apparatus that permits all healthcare providers, regardless of size and financial resources, to participate in clinically integrated networks in a cost-effective way that still meets the requirements of meaningful use Stage 2 and is scalable, flexible, and rapidly deployable without compromising quality or security. The same embodiments disclosed herein can be applied to different situations. One situation (or application) is related to the transfer of all patient records for switching from one Electronic Health Record (EHR) vendor to another EHR vendor. Each EHR vendor uses its own database with different data structure and often with encryption of sensitive patient data so it would not be easily used by other software. When a clinic moves from one EHR to another it is often left with old patient records residing in the old system and keeps both running for an extended period of time. The embodiments disclosed herein may be configured to automate the sending of all patient records one at a time from existing EHR to the new EHR (e.g., via Direct Messaging). Another use of the embodiments disclosed herein include automation of patient record extraction and transmission utilizing various functionality with the EHR's graphical user interface (GUI) in bulk or one patient at a time. Another use of the embodiments disclosed herein is related to the concatenation of patient records from diverse EHR's for group reporting of clinical quality measures and other financial data.

Similar to a CIN but with stricter requirements to report accurately when one owner owns/buys many clinics using different EHR's. One such example is Federally Qualified Health Centers (FQHCs) which have to report every year on patient statistics to qualify for federal funding. The U.S. Government requires FQHCs to submit their annual report in electronic format for ease of analysis. The interchange system and method of the current disclosure make it possible to generate quality reporting and population health. With the challenge of pulling data from diverse EHRs electronically, many FQHCs extract data manually and submit the reports via government website by hand, resulting in high labor costs and high error rates. In addition to enabling electronic global reporting for clinics with diverse EHRs, the embodiments disclosed herein allow for the submission of raw patient level clinical data automatically to regulatory bodies directly, allowing a higher level of analysis to be performed by U.S. Centers for Disease Control and Prevention as well as Centers for Medicare and Medicaid Services.

Another aspect of the embodiments disclosed herein is related to the transferring of clinical data from any MU2 certified EHR to specific registries and qualified clinical data repositories. Various government bodies (state, local, and federal) as well as professional organizations often require or desire clinics to report certain activities to a centralized registry. Examples include children's immunization registry, registry colon cancer registry, and human immunodeficiency virus (HIV). Certain state governments require Medicaid encounters to be reported to receive reimbursement. The embodiments disclosed herein allow a commercial interchange organization to receive clinical data from clinics automatically and then reformat the data into the type of interface specification required by government agencies. The interchange system and method of the present disclosure can pull from multiple sources and report in different data formats requested by different agencies (see FIG. 13). Hence, the interface can be maintained by one professional organization without each clinic to worry about maintaining the interface. Another aspect of the embodiments disclosed herein is related to the enablement of third party products to be used in conjunction with any clinic EHR. Currently it has been very difficult for third party vendors to gain access to sensitive patient data stored in proprietary database format to supply missing capabilities to clinic without paying expensive access fees and technical integration to the EHR vendor, in some cases direct database access is completely blocked by EHR vendor.

Another aspect of the embodiments disclosed herein is related to the automation of the transfer of needed information to the third party product and return any resulted information back to the clinic EHR. Examples of third party applications include clinical laboratories, annual wellness visits, chronic care management, behavior health integration, and transitional care management programs by Medicare.

Embodiments described herein may implement the interchange of data in CINs. In one embodiment described herein the extraction of data is done using data connectors, automated report reading, image analysis, and simulated user input such as by keyboard, mouse, and touch. The extracted information is transmitted to a centralized CIN data repository or directly entered into the other system. Embodiments herein may use image analysis tools, keystroke logging tools, and test automation tools to simulate user input to automate the transfer of all patient data successively at the beginning and update the CIN records when new patient data becomes available. One of the characteristics of this solution is using test automation tools to leverage the auditing, monitoring, error handling and alerts functionalities provided by these automation tools for extracting the data, thereby making the solution very robust.

The "front-end" interchange system and method described herein in some embodiments may receive new data at an EHR in a CIN, spin up (or start up) a virtual machine, contact through a virtual private network (VPN) the EHR, call up a record that has changed, use automated test tools to extract that data, and store the data in a Clinical Deposit Repository (CDR) where it can then be made available for reports and in other raw data formats. The interchange system and method disclosed herein may emulate users to access EHRs and instruct EHRs to export or write patient records to a "local disk". In alternative embodiments, an interconnection system may mount a virtual machine (with virtual disk drive) from a cloud service (e.g., Amazon Web Services) so the output will be directed to a datacenter. The automation software is based on software testing technology to emulate a human user running software repeatedly. By testing to seek errors, it is possible to cycle through patient lists to pull data records one-by-one.

Meaningful use (MU) requires limited elements of a patient record be included in a consolidated-clinical document architecture (C-CDA) of which some are machine readable and others only human readable. Many certified EHR vendors only include the minimum clinical elements required to attain certification. As a result, patient records produced as a C-CDA by the EHR do not contain sufficient clinical content for VBC. The interchange system and method of this disclosure leverages other methods available in graphical user interface (GUI) to gather data omitted in the C-CDA and then republishes an enhanced C-CDA with all necessary elements included as machine readable to be ingested by other EHR systems, CINs, or Health Information Exchanges.

Methods of extracting clinical information directly from an EHR database offer limited value for clinics that maintain their own EHR database server. Clinics who use a cloud based EHR are typically not permitted to directly access their own database with these tools and must rely upon limited functionality provided by the EHR vendor. An industry wide shift to cloud based EHR systems has significantly reduced physician and clinic functional access to their own clinical data. Clinics that maintain their own EHR database may be able to query and analyze clinical information directly from their database server, but usage and licensing restriction prohibit directly adding information to the database except through the application or approved interface.

As discussed, the interchange system and method described herein relates to the transfer of patient records from one Electronic Health Record (EHR) vendor to another EHR vendor, Clinical Data Repository (CDR), or government required registries for controlled substances or immunization. The interconnection system and method disclosed herein allows for the concatenation of patient records from diverse EHR's for group reporting of clinical quality measures. The interconnection system and method allows for transferring of clinical data from any government certified EHR to a specific registry. The interconnection system relates to the enablement of third party products to be used in conjunction with clinic EHRs. The CDR represents a permanent storage repository for the data collected. It is a permanent buffer between the data in the EHRs and the end users that need access to it.

FIG. 1 illustrates a prior art CIN with different EHR systems from different vendors. A CIN is defined as a plurality of health providers such as hospitals 100, specialists 110, post-acute facilities 120, independent providers 130, hospice care 140, ancillary provider 150, and physicians offices (or other participating entities) 160 that join together to improve care and reduce costs. The health providers are connected through a network 170 (e.g., the Internet). The network 170 includes at least one cloud based EHR vendor G190 which supports at least one physician's office 160.

FIG. 2A illustrates why healthcare data is so complex due to the many different elements and time history which are involved. EHR vendors A (200), B (210), C (220), D (230), E (240), F (250) and G (260) share information across the network 170 in a complicated manner. As discussed above, software that captures patient medical history is called EHR or EMR. The EHR industry has many vendors each with their own software.

There are currently at least two ways to achieve interoperability of systems. First, there is the HL7 which is a not-for-profit, American National Standards Institute (ANSI) accredited standards developing organization dedicated to providing a comprehensive framework and related standards for the sharing, integration, and retrieval of electronic health information that supports clinical practice and the management, delivery and evaluation of health services. "Level Seven" refers to the seventh level of the International Organization for Standardization (ISO) seven-layer communications model for Open Systems Interconnection (OSI)— the application level. The application level interfaces directly to and performs common application services for the application processes. Although other protocols have largely superseded it, the OSI model remains valuable as a place to begin the study of network architecture. HL7 interface is purchased via EHR vendors. HL7 takes a long time for an EHR vendor to install interface (e.g., 1.5 years) and can cost from $5K to $50K. Second, there is direct access to an EHR database. Direct access only works for on-premise EHR (not cloud based). It also cannot write back to EHR otherwise it would void the support contract. Referring to FIG. 2A, it shows that while HL7 is a standard, each vendor may have variations in how their software complies with the standard. This leads to constant maintenance of modules for many permutations (e.g., 42 modules for a small CIN). FIG. 2B illustrates direct access. The HL7 module permutations can be bypassed and data extracted from each EHR into a central database 270 if the data format from each EHR is known and there is the ability to unencrypt it (both of which are not likely).

These solutions however may lead to technical problems. A traditional HL7 interface is costly, often making it not economically viable. Traditional HL7 interface requires coordination of limited technical expertise among 2 or more vendors causing excessive implementation delay. Traditional HL7 interfaces do not accommodate technical modification. Technical modification such as application updates often break traditional HL7 interfaces. Compounded by additional coordination requirements with two or more vendors for the same technical resources causes frequent and excessive downtime which impacts clinical systems and patient care. Traditional HL7 Interfaces lack extensibility necessary to keep up with changes to practice operations and care delivery that payers such as Medicare and private insurers are demanding. Methods of extracting clinical information directly from an EHR database offer limited value for clinics that maintain their own EHR database server. Clinics who use a cloud based EHR are typically not permitted to directly access their own database with these tools and must rely upon limited functionality provided by the EHR vendor. An industry wide shift to cloud based EHR systems has significantly reduced physician and clinic functional access to their own clinical data. Clinics that maintain their own EHR database may be able to query and analyze clinical information directly from their database server, but usage and licensing restriction prohibit directly adding information to the database except through the application or approved interface.

FIGS. 2C and 2D also show another prior art alternative to solve the problem which is to use screen scraping. However, this is problematic as this solution needs to be reprogrammed if there is something as simple as a relocation of a data element in the underlying EHS program, such as the movement of the Patient Number field shown above, because screen scraping would be programmed to go to a given (x,y) coordinate on the screen. However, once the field moves, the (x,y) coordinates change. There can also be issues with Optical Character Recognition (OCR) technology to properly read information from the screen image.

FIG. 3 illustrates an improved interchange system and method 370 over that of the prior art. A CIN 300 is shown with a plurality of health providers located at a plurality of nodes such as EHR Software Vendor A (hospital) 302, EHR Software Vendor B (specialist) 310, EHR Software Vendor C (post-acute facility) 320, EHR Software Vendor D (independent provider) 330, EHR Software Vendor E (hospice care) 340, EHR Software Vendor F (ancillary provider) 350, and EHR Software Vendor G (physicians offices) 360 that join together to improve care and reduce costs. The health providers are connected through network 380. Connecting network 380 may be any type of Wide Area Network (WAN), such as the Internet, Local Area Network (LAN), or the like, or any combination thereof, and may include wired components, such as Ethernet, wireless components, such as Long Term Evolution (LTE) or Wi-Fi, or both wired and wireless components. The connecting network 380 includes at least one cloud based EHR vendor G 390 which supports at least one physician's office 360. Cloud-based refers to applications, services and/or resources made available to health providers on demand via the network 380 from cloud computing servers (e.g., EHR cloud vendor 390). The interchange system 370 may reside on a server with an accompanying database as shown in FIG. 3. Note that while the server in FIG. 3 is illustrated as an individual single server, the interchange system and method 370 may alternatively be distributed across multiple servers having the respective functionality of the single server. The servers may be located a central location or at a plurality of locations. And still in other embodiments, the computers at each healthcare provider in the CIN (302, 310, 320, 330, 340, 350, 360 and 390) may also be combined into one single server or distributed across multiple servers having the overall combined functionality of these computers to form interchange system and method 370.

FIG. 4 is an illustration of high level deployment architecture of the interchange system and method 370. A "smart agent" 408 of the interconnect system and method 370 described herein does not require installation of software or hardware on each clinic's systems to operate. The smart agent 408 does not require coordination with other vendor resources which can significantly accelerate implementation from months to days. The smart agent combined with its "conductor" 410 is further configured to accommodate application changes, reduce downtime and proactively anticipating code updates for other clients. The smart agent 408 is capable of delivering the agility and extensibility necessary for healthcare organizations to identify care gaps, quality measures, and clinical quality improvement programs that are part of modern care delivery. The smart agent 408 is configured to quickly adapt to the inevitable changes in requirements that will face healthcare in the future.

Data reporting and collection functionality provided by EHR software vendors varies widely from one solution to the next. Most are not configured to produce data that meets the reporting and operational needs of provider organizations. The smart agent 408 is configured to overcome these obstacles by gleaning data from any and all sources available in the EHR system then combining the required information into a platform that meets the provider organization's needs. By providing complete and timely clinical information in a consumable format, the smart agent 408 increases data value. Unlike other methods that can only read information or write limited information back to the EHR, the smart agent 408 is able to add any information to any location of the EHR. The smart agent 408 makes valuable data actionable data to improve care delivery and care quality.

Referring to FIG. 4, conductor 410 coordinates the integration with different EHRs' such as 302, 310, 320, 330, 340, 350, 360, and 390. Conductor 410 has capabilities like scheduling, auditing, monitoring, creating alerts and/or error handling. Automation workflow engine 412 may host the automation scripts (or components). Automation workflows are a number of sequences/steps that are executed to retrieve the targeted data from the EHR clinic. Automation workflows may be configured for maximum reuse and rapid, widespread deployment. Automation script(s) (or components) are a set of instructions that will be performed on the interchange system 370 to test that the system functions as expected. Automation scripts are the set of instructional commands that go with the automated testing tools to find patient records in an EHR and extract the data. The scripts also include information for logging in to a particular location. For example: Virtual Private Network (VPN) to an Internet Protocol (IP) address or hostname; for the credentials used to get in questions such as how do they keep the credentials safe or how do they sync the credentials when they are changed are resolved and once in, this is how the EHR system is launched; how to get logged into the system; how to search on a patient record; how to call up the screen; how to pull out the information; and how to save to a local disk.

As will be discussed in connection with FIG. 8, "reusable scripts" (or "reusable components") is a different way of considering automation scripts. Specific variables such as a VPN IP address or user name are maintained in the practices configuration and then called by the automation script as needed. Script titles might be something like the following. First, start VPN. Second, start EHR. Third, get appointment list. Fourth, get C-CDAs for each. The automation workflows are configured for maximum reuse and rapid, widespread deployment. Hub 414 is a central location where automation script requests are accepted and distributed onto the plurality of nodes EC2 located at each of the EHRs (i.e., 302, 310, 320, 330, 340, 350, 360, and 390 in FIG. 3) where the automation scripts are executed. Alternatively, these nodes EC2 may be virtual machines that are located at the cloud vendor (e.g., Amazon Web Services (AWS)) and that may be spun up dynamically as needed. Automation scripts perform specific packages (or jobs) within a target system or application. Examples of automation scripts are the following: start EHR, extract daily lab orders, or Insert GAPs in Care Reminders. Automation scripts are configured for specific systems for maximum reuse with clinic specific data maintained in a configuration. By example an automation script configured to extract daily lab orders in the eClinical Works EHR version 10 (version 10 (v10)) will work for all practices with eClinical Works EHR v10. If a medical practice using the same EHR is configured differently is may require minor adjustments to the automation script. The interchange system 370 is configured to permit survival of practice specific modifications during code updates. The interchange system 370 maintains the automation scripts for maximum reusability and minimum downtime across all integrations. By example, if one practice is updated from eClinical Works v10 to v11 causing an automation script to fail, the root cause will quickly be assessed and a solution configured to accommodate both v10 and v11. By deploying this solution to all clinics using the automation script, practices upgrading from v10 to v11 in the future will not experience downtime (see discussion of FIG. 8 and FIG. 9).

The nodes EC2 make up an auto scale group 418 wherein the number of nodes EC2 connected to the hub 414 will depend on the load on the hub 414. The nodes EC2 can be started and stopped based on the load. Unlike other automation solutions, in some embodiments, the smart agent 408 and conductor 410 may be 100% cloud based and do not require installation of any agent or software on the clinical system. This approach improves scalability by reducing support requirements and avoiding potential system incompatibility issues. The smart agent 408 may be located independently of the nodes EC2 at the main interchange system server 370 or located in a node EC2 (or a plurality of nodes EC2). The smart agent 408 checks in with the conductor 410 on the main server 370. Each node EC2 has the ability to interface with the local network and local resources of the particular provider. Each EHR provider (e.g., 302, 310, 320, 330, 340, 350, 360, and 390) has a node EC2 with a smart agent 408, and the smart agents 408 feed the data back to the main system 370.

A triggering of a data extract starts at the conductor 410 either through a schedule process or through an actionable item that will trigger the data extraction request. Once the conductor 410 determines which script to execute it will send a request to the automation workflow engine 412 which packages all the necessary artifacts that are needed to execute the automation script and forward the request to the hub 414. An artifact is one of many kinds of tangible by-products produced during the development of software. Some artifacts (e.g., use cases, class diagrams, models, requirements and configuration documents) help describe the function, architecture, and configuration of software. Based on the predefined requirements that are described in the automation scripts artifacts, hub 414 will determine the type of the node of the plurality of nodes EC2 for executing the automation workflow and then forward the request to one of those available nodes EC2. The hub 414 provides a guaranteed delivery option in case the nodes EC2 are not available or connection between the hub 414 and a node EC2 is lost the hub 414 will retry until it gets a success response. FIG. 4 further shows file system 416 which is a Clinical Data Repository (CDR) (or Clinical Data Warehouse (CDW) or just "repository") employed in the interchange system 370.

The "front-end" approach used for the interchange system 370 emulates a user's access to EHRs and instructs the EHRs to export or write patient records to a "local disk". The terms front end and back end refer to the separation of concerns between the presentation layer (front end), and the data access layer (back end) of a piece of software, or the physical infrastructure or hardware. In the client-server model, the client is usually considered the front end and the server is usually considered the back end, even when some presentation work is actually done on the server itself. A front-end interface inherently reduces certain integration and licensing costs. The interchange system 370 is capable of mounting a virtual machine (with a virtual disk drive) from a cloud server (e.g., Amazon Web Services (AWS)) so the output will be directed to the datacenter associated with server 370. The automation software is based on software testing technology to emulate a human user running software repeatedly (e.g., testing to seek errors the system will cycle through a patient list to pull data one-by-one).

FIG. 5 shows a high level flow of the interchange system 370. The test automation tools associated with the automation workflow engine 412 leverage the auditing, monitoring, error handling and/or alert functionalities for integrating with different EHRs' and thereby making this type of integration reliable, scalable and maintainable. The interchange system 370 may copy data from a website (e.g., screen scraping) to extract data. The interchange system 370 primarily simulates a user via a testing tool to invoke the EHR software and click on commands that output the data that is desired. A virtual machine may be provided by a cloud-based datacenter (e.g., AWS) to simulate a user asking EHR to export data into a "local disk" (all can do that as typically that is required to be certified), where the "local disk" is actually storage in cloud-based (e.g., AWS) data center. The above is captured in test scripts to repeat over a population or fixed duration. The above approach still may not be reliable as a screen can pop up and as well as other unstable issues with the EHRs. To make it scalable, the data extraction code of the interchange system 370 will wake up at pre-fixed intervals and download instructions from conductor 410. If a network of physicians change requirements all members of the network 300 will get the new instruction if a subset of the network using a particular EHR vendor who modify their graphical user interface (GUI) and all users of that EHR will be updated by loading the right scripts.

FIG. 5 illustrates a flowchart of the method or process of the interchange system and method 370. In step 502, the conductor 410 receives a trigger event (e.g., specific time of day, request or wake up, completion of a previous package in the queue). In step 504, conductor 410 determines a package to execute. A package is a selected make up of a sequence of scripts. Types of scripts may include the following: start VPN, start EHR, get appointment list, and/or get C-CDAs for each. In step 506, conductor 410 sends a request to automation workflow engine 412. In step 508, automation workflow engine 412 packages the necessary scripts (or components). In step 510, automation workflow engine 412 sends the package (i.e., workflow) to hub 414. In step 512, the hub 414 determines a type of node EC2 for executing the package. In step 514, the hub 414 retries until it can deliver the package to a node EC2. In step 516, the node EC2 executes the workflow. In step 518, data from the node EC2 is updated in the repository 416.

FIG. 6 illustrates the details about the structure and operation of an exemplary node EC2 accessing an on-premise EHR and FIG. 7 illustrates a cloud based EHR instead of an on-premise EHR. Once the hub 414 forwards the request to a node EC2, the node EC2 will start executing (step 601) the automation workflow 600. Each node EC2 is protected by a firewall. The conductor 410 maintains communication with the process throughout its execution. The heartbeat 610 is the timely expected response from the processing node EC2. The hub 414 does the same with regards to the node EC2 exclusive of an active process. In case of an on premise EHR the connection to the remote host 602 is established (step 603) using a virtual private network (VPN) client 604 so as to maintain a secure connection. Once the connection is established (step 605) the automation will send various commands to the EHR client 606 installed on the remote host 602. Remote data protocol (RDP) in FIG. 6 may be used to connect to the EHR system. At each step of the automation flow, the node EC2 communicates with the conductor 410 before the beginning of the step and after completion of the step. This kind of communication between a node EC2 and the conductor 410 helps to improve process reliability, data quality, and expedite the corrective action if needed. The data from remote host 602 is extracted in step 607.

Referring to FIG. 7, in the case of a cloud based EHR the communication will happen using a browser 611. Athena 612 in FIG. 7 is a cloud based EHR. The rest of the process will be the same as described in connection with FIG. 6.

FIG. 8 illustrates the automation workflow in automation workflow engine 412 discussed above in more detail. Automation workflows are a number of sequences/steps that are executed to retrieve the targeted data from the EHR clinic. The interchange system and method 370 will use a script (or component) based architecture while building these automation workflows. Each automation workflow is broken into its smallest possible script (or component) so they can be reused in other similar automation workflows. FIG. 8 shows how to launch a particular VPN to get to the CIN member's network, then how to launch this particular EHR system, then how to get this particular window in the EHR system.

FIG. 9 illustrates the structure of the file system of repository 416 which is the workflow and script repository 416 discussed above in connection with FIG. 4 which is used in the interchange system 370. The repository 416 contains the source and executables for the workflows and their scripts (or components). The repository 416 is configured for maximum reuse and rapid, widespread deployment. FIG. 9 further shows examples of how scripts are assembled into a package or workflow. It shows how some scripts (or components) are common, some are specific to a practice, and some are version specific.

FIG. 10 shows how a smart agent 408 and the conductor 410 coordinate. It is common for an application version change to break a traditional HL7 integration used in daily clinical operations for weeks to months. The interchange system 370 builds application version monitoring into every connection. If a version change requires any changes to a process, it allows for the ability to quickly make corrections. This also enables the ability to proactively apply changes as other clients apply the same updates completely avoiding downtime. Ability to conduct detailed analysis of customer modifications, additions, and trends have been configured into the interchange system 370 solution from inception. Usage and trends analysis enable the interchange system 370 to proactively update default settings of current products and provide guidance for solution development and improvement. In step 1002, the smart agent 408 obtains attribution lists from a payer or practice. An attribution list is a list of patients meeting certain attributes such as age, insurer, or diagnosis. In this case certain insurers offer value based incentives to provider for their insured patient population. The insurer is not permitted to receive patient data except for their customers. To assure only these patients are selected, an attribution list is provided by the insurance payer. The smart agent 408 then checks in with the conductor 410 (step 1004). In step 1006, the smart agent 408 obtains additional patient lists based on clinical quality measures or provider specified analytics. The smart agent 408 then checks in with the conductor 410 (step 1008). In step 1010, the smart agent

408 then assigns processes for each patient on a combined list and then checks in again with the conductor 410 (step 1012).

The interchange system 370 will frequently audit for quality. FIG. 11 shows a flowchart 1100 illustrating error handling between the smart agent 408 and the node EC2. Each integration is comprised of many reusable scripts and each script may contain several logging points which are updated to the conductor 410 as each package is executed. Prior to starting a package, the conductor 410 collects all expected log point sand timeouts. In the event of an error or system failure, the conductor 410 is able to immediately override the package and notify support. Expected scripts also include known data such as patient ID numbers, where the results received from the smart agent 408 are compared to expected results, further ensuring data quality. In step 1102, a smart agent 408 and node EC2 are assigned. In step 1104, assignment is confirmed and send step detail is expected in a log. The node EC2 replies back confirming it has accepted the package and reads back the detailed instructions for confirmation. In step 1106, the smart agent 408 and node EC2 may be reassigned if not confirmed. In step 1108, if not as expected after actions logged and patients completed (step 1110) then either force close smart agent 408 (step 1110) or if smart agent 408 fails or times out (step 1114), then delay and restart as configured (step 1116). If there is an error or not complete (step 1118) then a support ticket is posted (1120). Running in parallel, after assignment is confirmed in step 1104, the assigned packages are started (step 1122). If an error (step 1124), a log error of a screen shot is reset and retried (step 1126) and if error (step 1128), then log error screenshot and close client node (step 1130) and log successful completion (step 1132). Note that the conductor 410 may restart smart agent 408 at any point in the package process with or without delay based on the error handling logic and then resume at the last successful compilation. Referring to FIG. 11, the conductor 410 can detect problems with a smart agent 408 and force the smart agent 408 to close and restart if there is trouble receiving data from a particular EHR provider. In some embodiments, conductor 410 communicates with a smart agent 408 that may reside in a virtual machine that has the ability to communicate through a virtual private network (VPN) with the EHR provider's network and then RDP to a resource where the EHR can be accessed to extract data. The interchange system 370 can then write that data to the storage in the virtual machine, but then transfer it more permanently to the repository 416 so that the data can then be shared with other EHR providers.

The interchange system and method 370 will also audit for completeness and reconcile actual changes to expected changes to ensure that all updates to patient information are captured and accurately applied. Depending on the nature of each automation script, data entry is reconciled both at the individual transaction level and package level through the clinical system's user interface. A problem is that updated patient information enters the EHR sporadically either before or after the date of an encounter. Patient information updates provided by the audit function of various EHR vendors has proven incomplete. As a resolution, the interchange system 370 includes monitoring multiple points of data entry and audit logs to detect updated patient information. Daily updates include comparing the current state of historical EHR data to an update log assuring pre-dated patient information is captured.

FIG. 12 shows a detailed block diagram of the repository 416 first discussed in FIG. 4. Data is received by the repository 416 from a plurality of different sources. A first source is the registry 1202. A registry could be an immunization registry or controlled substances registries. A second source is the EHR report 1204. A third source is the Unified Consolidated Clinical Document Architecture (CCDA) format 1206. The CCDA for Meaningful Use Stage 2 is a flexible markup standard developed by HL7 that defines structure of medical records to facilitate interchange between providers & patients. A fourth source is the EHR/ Practice Management (PM) screen. A fifth source is through an application programming interface (API) 1210 for exchanging health records like a web service. A sixth source is HL7 Fast Healthcare Interoperability Resources (FHIR) (which is pronounced "fire") 1211 which is a draft standard describing data formats and elements (also known as "resources" or "nodes"). The standard was created by the Health Level Seven International (HL7) health-care standards organization. FHIR builds on previous data format standards from HL7, like HL7 version 2.x and HL7 version 3.x. But it is easier to implement because it uses a modern web-based suite of API technology, including a HTTP-based representational state transfer (RESTful) protocol, hypertext markup language (HTML) and Cascading Style Sheets for user interface integration, a choice of Javascript Object Notation (JSON), Extensible Markup Language (XML) or resource description framework (RDF) for data representation, and Atom for results. One of its goals is to facilitate interoperation between legacy health care systems, to make it easy to provide health care information to health care providers and individuals on a wide variety of devices from computers to tablets to cell phones, and to allow third-party application developers to provide medical applications which can be easily integrated into existing systems. FHIR provides an alternative to document-centric approaches by directly exposing discrete data elements as services. For example, basic elements of healthcare like patients, admissions, diagnostic reports and medications can each be retrieved and manipulated via their own resource uniform resource locators (URLs). FHIR was supported at an American Medical Informatics Association meeting by companies like Cerner which value its open and extensible nature.

Referring still to FIG. 12, these plurality of input sources provide data to block 1212 which is mapping the received data to a common data format. The repository 416 of the interchange system 370 then stores as mapped standard data 1214 and non-standard data 1216. The repository 416 can then deliver the standard data 1218 in custom mapped outputs 1220 for different ultimate goals—such as to delivering data to an EHR 1222, delivering data to an analytics engine 1224, delivering data for quality reporting 1226, and/or to deliver data for population health management reporting (aggregation of patient data cross multiple health IT resources into an actionable patient record for identifying actions for improving clinical and financial outcomes) 1228.

FIG. 13 is similar to FIG. 12 except in FIG. 12 it is shown how the repository 416 of the interchange system 370 can be used and FIG. 13 shows the way data can be delivered including directly to the EHR system 1222, in a flat file 1224 (a flat file may be a text file with no data structure), in FIHR format 1226, in a CCDA format 1228, and through an API (e.g., web service) 1230.

FIG. 14 shows the inputs 1400 into the repository 416 by registry 1202, EHR report 1204, CCDA 1206, and EHR/PM Screen 1208. Smart agent 408 accesses necessary data elements from various sources. Each data source may include unique credentials, unique technology, and access to data that is not support by traditional APIs. There are increasing demands on clinical data such as performance based compensation, quality measures, quality improvement, patient safety, aggregated reporting, and regulatory reporting. Traditional clinical integration methods lack both flexibility and agility needed to acquire the clinical information necessary to meet the demands of high performing healthcare provider organizations.

FIG. 15 shows visual data mapping 1500 which is how the interchange system 370 takes the input and maps it into the repository 416. Simulated forms or screens from each EHR can be completed by the smart agent 408. A default mapping of common fields is completed by the interchange system 370, but additional custom data can be added from the repository 416 at the practice level with a simple drag and drop. Form building technology allows customers to make changes to which data elements are selected and where the specific data elements are inserted into their system. Imported data is often too verbose or includes elements the provider as a matter of preference would like to omit. By coupling forms mapping technology 1502 with smart data, providers and end users are able to make preference changes to information that is imported to their system without the wait or expense of technical support.

FIG. 16 illustrates how the data is then pulled out of the repository 416 and formatted for delivery to the client EHR. Smart data is pulled from any source, by any method, and for any type. Through implementation of a smart process, common workflows are available by default and customizable at the practice level.

FIG. 17 is an illustration of how the interchange system 370 makes common workflows available to medical practices by default for common data elements, but medical practices can customize their own workflows for additional data not covered, simply by clicking the desired field and drag and drop. Workflow automation extends beyond entry in the EHR to every application in a process. Enter and extract information may be in the same workflow. Enter and extract is possible for any data element in the smart data registry 1202. FIG. 17 illustrates that the interchange system 370 can enter and extract information and/or any element in the data registry 1202 in the same workflow. In other words, when interchange system 370 contacts, for example, a primary care physician's EHR, while it may be updating data for that practice based on updates from a specialist's practice (i.e., a patient visited a specialist and notes are updated from the specialist in the primary care physician's EHR), the interchange system 370 is also extracting updates from the primary care physician's EHR for the interchange system repository 416.

FIGS. 18 and 19 illustrate how a screen labeled 1800 may change for a particular EHR vendor between versions. However, by using automated testing tools, as long as the field names are retained, the workflow automation scripts will continue to work fine. For example, EHR Vendor A has a screen N of data with field elements W-Z (maybe patient first name, middle name, last name, and suffix) in two versions of the software C & D. Because the field names are unchanged between versions, interchange system 370 automation scripts will still work and can populate or extract this data.

FIGS. 20A and 20B illustrate how screen 1800 may change for a particular EHR vendor between versions and new field elements are added. In this case, interchange system automation scripts will error if the new field has been requested or supplied and it is not in the script. At this point, interchange system 370 will be notified of the script failure, and manual intervention by interchange system 370 will be needed. But once interchange system 370 updates the script for the new field, it is available for all practices who have moved to that new version. For example, EHR Vendor A has a screen N of data with field elements W-Z (maybe patient first name, middle name, last name, and suffix) in two versions of the software C & D. In version D, the Vendor A has added new field V to handle the title for the patient (Dr., Mr., Mrs., Miss, etc.). Because the new field V was not in the software before, any requests for or data supplied for that field will break the Interchange system's script until it can be updated. But once updated, with the common architecture of workflow scripts (or components), the field is effectively updated for all practices when they move to that new version.

FIG. 21 illustrates one type of work flow 2100 for the interchange system and method 370 for a multi-system organization similar to one shown in FIG. 3. This workflow example is for ongoing clinical data extraction from EHR and Practice Management (PM) systems that is inserted (step 2102) into a Health Information Interchange (HIE), Population Health Vendor, or used by a clinic to meet regulatory reporting requirements, backup and business continuity requirements, or migration other clinical systems. Boxes 2200, 2300, 2400, 2500. 2600, 2700, and 2800 reference the interchange system 370 technical solution to the technical problem.

FIG. 22 shows specific technical solutions (step 2200) to technical problems of the workflow in FIG. 21. Process 2200 is a scheduled update of select patient information illustrating coordination of the conductor 410 and smart agent 408. In step 2202, there is a scheduled process from the conductor 410. The conductor 410 identifies patent, practice, and checks for updated patient data. In step 2204, the system checks to see if the list is empty? If yes, the flow concludes (step 2206). If not empty, it reviews the automation scripts (step 2208). In step 2210, the hub 414 identifies empty nodes EC2 and distributes work. In step 2212, at node EC2, smart agent 408 carries out a function. In step 2214, VPN is started. In step 2216, the RDP is connected. In step 2218, login and find patient, select patient data, copy, and send back to conductor 410. The process repeats back to step 2202.

Referring back to FIG. 21, in step 2104 is a CCDA care summary. In step 2106, reports, patient history, procedures, lab results, and diagnoses. In step 2108, HIE consent, screening, questionnaire, and results. This information is all forwarded to the repository 416 in step 2214.

FIG. 21 shows a step 2300 and FIG. 23 shows step 2300 in detail. Process 2300 is a scheduled update of select images illustrating coordination of the conductor 410 and smart agent 408 with the ability to retrieve non-discrete data. Step 2300 is same as step 2200 except in step 2302 in the scheduled process from conductor 410 as described in relation to step 2202, the system checks for previously saved images for new ones. Steps 2304, 2308, 2310, 2312, 2314, 2316, and 2318 are then similar to those in step 2200. Returning to FIG. 21, the images and scanned documents are attached to patients chart in step 2110 and forwarded to repository 416.

FIG. 21 shows a step 2400 and FIG. 24 shows step 2400 in detail. Process 2400 is the triggered update of financial or payer data associated with a patient. Technical problem is automating how a third party receives updated insurance to process a claim. The automation can be triggered by a third party event such as claim denial. In step 2402, there is a trigger event and the conductor 410 starts, identifies patient practice and determines if financial information has changed. Steps 2304, 2308, 2310, 2312, 2314, and 2316 mimic those of step 2200. In step 2318, the system 370 finds new financial information, makes a copy, converts it to a specified format, and sends to conductor 410 to save in repository 416.

Referring to FIG. 21, after step 2114 there is step 2500 which is detailed in FIG. 25. In step 2502, the repository 416 is checked to see if the information exists. In step 2504, the C-CDA/CCD adapter has the ability to receive CDR data in a C-CDA or CCD format and convert it to a format that can be consumed by other systems through the Interchange portal (step 2506). Referring to FIG. 21, an enhanced CCDA XML file (step 2116) is forwarded to a health information exchange 2118 and PoP Health database (step 2120).

Referring to FIG. 21, after step 2114 there is also a step 2600 which is detailed in FIG. 26. In step 2602, the repository 416 is checked to see if data exists. In step 2604, the CSV/Text Adapter has ability to receive repository data in flat file such as CSV or text and convert it to a format than can be consumed by other systems through the Interchange portal (step 2606). Referring to FIG. 21, a CSV file format (step 2122) is also forwarded to a health information exchange 2118 and PoP Health database (step 2120).

Referring to FIG. 21, after step 2114 there is a step 2700 which is detailed in FIG. 27. In step 2702, the repository 416 is checked to see if data exists. In step 2704, HL7 Adapter shows ability to receive an HL7 formatted and convert it to a format that can be consumed by other systems through the interchange system 370 portal (step 2706). Referring to FIG. 21, a HL7 V2 format (step 2124) is also forwarded to a health information exchange 2118 and PoP Health database (step 2120).

Referring to FIG. 21, after step 2114 there is a step 2800 which is detailed in FIG. 28. In step 2802, the repository 416 is checked to see if data exists. In step 2804, API adapter shows ability to receive data directly from a source such as a repository 416 through a web API such as Rest. Then convert it to a format that can be consumed by other systems through the interchange system 370 (step 2806).

Referring to step 21, after 2800, interchange system 370 platform and portal is connected to EHRP PM Migration 2132, Unified Reporting (Quality Measurements UDS Value-Measured) 2134 and standby EHR and backup 2136.

FIG. 29 shows one type of work flow 2900 for a billing integration for a CIN 300 such as the one shown in FIG. 3. This is a typical workflow for two methods of an ongoing medical billing integration from a disparate clinical system to practices billing system. In step 2902, practice provider patent and payer data is provided as a discrete practice provider, demographic, and payer data (step 2904). The interchange system 370 platform and portal having CCM, AWV, and BHI provides discrete encounter data (step 2906). In step 2908, there is a translation and match with patient and provider process. In step 2910, configure data elements for encounter and change batch creation in EHR/PM. In step 2912, create encounter, insert clinical data, and then encounter ready for sign off. In step 2914, EHR message and encounters ready for approval. In step 2916, encounter based billing and in step 2918, claims data. In a parallel path, step 2920, create change batch. In step 2922, attach CCD or document to chart. In step 2924, EHR message: update summary and change batch is ready for approval. In step 2926, change batch received and submitted and in step 2918, claims data. Step 2920 is a reconciliation step which then feeds back to interchange system 370 portal and platform.

FIG. 30 references block 3000 in FIG. 29. In step 3002, starting the process with a scheduled task, event trigger (i.e., update) and on demand. In step 3004, conductor 410 identifies all the systems from location of data that needs to be pulled. In step 3006, are all systems pulled? If yes, in step 3008, conductor data is transformed to generate master file. In no, in step 3010, involve automation script. In step 3012, extract data. In step 3014, send to conductor 410 and return to step 3006.

FIG. 31 references block 3100 in FIG. 29. In step 3102, the CSV Adapter has ability to receive data from the repository 410 and convert it to a format than can be consumed by other systems through the interchange system 370 portal (step 3106).

FIG. 32 shows how the conductor 410 and smart agent 408 coordinate specific data such as clinical orders bidirectionally with a third party vendor such as a laboratory. In general traditional clinical laboratory to EHR interfaces take too long to implement and cannot effectively scale for smaller local or regional laboratories to implement effectively. The flexibility and short implementation cycle of the interchange system 370 solution enables clinical laboratories to integrate with their client's EHRs. Certain specialty laboratories such as those providing pharma genetic services require clinical information that is not included with most traditional EHR interfaces. Interchange system 370 technology enables bi-direction information sharing of the specific clinical and practice management these specialty laboratories require without increasing operational burden on the practice.

FIG. 32 shows in step 3302 a clinic a lab order created in EHR which includes a sample tracking number. In step 3304, the interchange system 370 retrieves and logs lab orders. In step 3306, the interchange system 370 retrieves processing information (e.g., patient CCDA, demographics, and payer information). Most CCDA information varies by EHR and practice. Most CCDAs provided demographics current medications, drug allergies, diagnosis, problem list, and payer information. Of these payer information is most commonly omitted from or is not current in the CCDA. Medication information is typically included, but is not coded. In step 3208, at the lab, lab results are provided as PDF associated with EHR lab order number and patient identification (ID) from EHR. In step 3210, the interchange system 370 inserts lab results in EHR associated with EHR lab order number. Update order status to results for review. In step 3212, at the clinic, the lab results are reviewed in EHRs.

FIG. 33 shows the basic hardware elements of a general computing device (server, PC, phone, tablet, etc.) upon which the interchange system and method 370 may operate. Embodiments described herein implement the exchange of data in clinically integrated networks (CIN). One embodiment involves the extraction of data using data connectors, automated report reading, image analysis, and simulated user input such as keyboard, mouse, and touch. According to embodiments disclosed herein, the extracted information is sent via Direct Messaging for transmission to a centralized CIN data repository or directly entered into the other system. While Direct Messaging has exclusively been used to manually send data one patient at a time when needed to other clinics (e.g., referral to specialist), embodiments herein use image analysis tools and keystroke logging tools and test automation tools to simulate user input to automate the transfer of all patient data successively at the beginning and update the CIN records when new patient data becomes available. While Direct Messaging is a convenience and a government preferred method of transferring clinical data, the current innovation also applies to transport clinic data via standard secured FTP, which requires some manual setup but can be faster in transfer speed. The data in a CIN is generally exchanged between computers.

FIG. 33 illustrates hardware components in a computer in the CIN according to embodiments disclosed herein. The device 370 of FIG. 33 includes a processing system 3310 that includes one or more processors 3311, such as Central Processing Units (CPUs), Application Specific Integrated Circuits (ASICs), and/or Field Programmable Gate Arrays (FPGAs), a memory controller 3312, memory 3313, which may include software 3314 such as the type described herein, and other components that are not shown for brevity, such as buses, etc. The processing system may also include storage 3315, such as a hard drive or solid-state drive. The processing system 3310 also includes a peripherals interface 3316 for communicating with an input/output (I/O) subsystem 3340, which includes a display(s) controller 3341 operative to control display(s) 3342. In some embodiments the display(s) 3342 is a touch-sensitive display system, and the display(s) controller 3341 is further operative to process touch inputs on the touch sensitive display 3342. The I/O subsystem 3340 may also include a keypad(s) controller 3343 operative to control keypad(s) 3344 on the device 370. The I/O subsystem 3340 also includes an optical sensor(s) controller 3345 operative to control one or more optical sensor(s) 3346. The optical sensor(s) may include, but is not limited to, a camera and an image sensor. In some embodiments, the I/O subsystem 3340 also includes a pointer device(s) controller 3347 operative to control one or more pointer device(s) 3348, such as a mouse or navigation shuttle. In yet other embodiments, the I/O subsystem 3340 also includes a keyboard(s) controller 3349 operative to control one or more keyboard(s) 3350. The peripherals interface 3316 may also communicate with other components of the device 370, including but not limited to, radio frequency (RF) circuitry 3352, such as Wi-Fi and/or cellular communications circuitry such as wireless Ethernet, LTE, Bluetooth, and near field communication (NFC), audio circuitry 3354 for the audio input component 3353, such as a microphone, and audio output component 3355, such as a speaker, one or more accelerometers 3356, one or more other sensors 3358, such as a location determination component such as a Global Positioning System (GPS) chip, and one or more external ports 3360, which may be used for smart card readers or for wired connections such as wired Ethernet, USB, or serial ports. The RF circuitry 3352 and external ports 3360 individually and collectively make up the communication interfaces for the device 370. The processing system 3310 is also connected to a power system component that is used to power the device 370. The processing system 3310 is also connected to a power system component 3320 that is used to power the device 370, such as a battery or a power supply unit. The processing system 3310 is also connected to a clock system component 3330 that controls timing functions.

FIG. 34 shows the basic elements of a Virtual Machine 3400 implementing the interchange system and method 370. Virtual machines 3406, 3416 and 3424 may be the nodes EC2. These virtual machines allow the smart agents 408 to receive instructions from the conductor 410 and interface with the EHR providers to extract data. The virtual machines (3406, 3416, 3424) each have a guest operation system (3408, 3418, 3426), smart agents 408 and EHR software vendors (3412, 3422, 3432).

Technical problems solved by the interchange system 370 include the following. A front-end interface inherently reduces certain integration and licensing costs. The interchange system 370 does not require installation of software or hardware on the systems of the clinics (e.g., 310, 320, 330, 340, etc. of FIG. 3) to operate. The interchange system and method 370 does not require coordination with other vendor resources (or nodes), significantly accelerating implementation from months to days. The conductor 410 of the interchange system 370 is configured to accommodate application changes, reduce downtime and proactively anticipate code updates for other clients. The interchange system 370 is configured to deliver the agility and extensibility necessary for healthcare organizations to identify care gaps, quality measures, and clinical quality improvement programs that are part of modern healthcare delivery. The interchange system 370 is further configured to quickly adapt to the inevitable changes in requirements that will face healthcare in the future. Data reporting and collection functionality provided by EHR software vendors varies widely from one solution to the next. Most are not configured to produce data that meets the reporting and operational needs of provider organizations. The interchange system and method 370 is configured to overcome these obstacles by gleaning data from any and all sources available in the EHR system 300, then combining the required information into a platform that meets the provider organization's needs. By providing complete and timely clinical information in a consumable format, the interchange system 370 increases data value. Unlike other methods that can only read information or write limited information back to the EHR, the interchange system 370 is able to add any information to any location the EHR system 300. The interchange system 370 makes valuable data actionable data to improve care delivery and care quality.

Technical problems further addressed by the interchange system and method of this disclosure may include the following. First, as discussed, a traditional HL7 interface is costly which often makes it not economically viable. Second, a traditional HL7 interface requires coordination of limited technical expertise among two or more vendors causing excessive implementation delay. Third, traditional HL7 interfaces do not accommodate technical modification. Fourth, technical modifications such as application updates often break traditional HL7 interfaces. Fifth, compounded by additional coordination requirements with two or more vendors for the same technical resources causes frequent and excessive downtime which impacts clinical systems and patient care. Sixth, traditional HL7 interfaces lack extensibility necessary to keep up with changes to practice operations and care delivery that payers such as Medicare and private insurers demand.

Another challenge facing the value-based care (VBC) model for healthcare involves the reconciliation and/or incorporation of data from new healthcare technologies. The Covid-19 pandemic, among other factors, drove additional innovations in healthcare technology. A lot of health information technology (IT) vendors have emerged with products like Remote Patient Monitoring, Telehealth, and Care Management. These are third-party software applications that are separate from the primary EHR system that houses the patient's primary medical information. These third-party applications bring tremendous value to patient care. However, it can be a challenge to get a comprehensive view of the patient health information when information from these disparate third-party applications are separate from the EHR system. Further, the workflow of working both in the EHR system and the third-party software applications is not streamlined.

EHR users in the clinics typically interact with their EHR through a simple web browser, like the Google Chrome browser and the like. EHR users are reluctant to log into any third-party applications that need to open up a new tab in the browser because they have to enter their credentials for the the third-party application with each access and it ends up adding a lot of steps to the clinic workflow thus impacting the time spent on patient care (i.e., the EHR users have to enter the credentials for each third party application, search for a patient record and then synthesize the data between the systems). This awkward interaction and workflow could be improved by leveraging technologies (like single sign-on) that allow EHR users to easily get access to the third-party software applications without always having to enter their credentials for each interaction with those applications.

However, to accomplish this, each EHR vendor would need to natively support single sign-on for each of the respective third-party applications (i.e., EHR vendors would have to build the single sign-on functionality for each third-party application for Telehealth, etc. via a button or comparable mechanism). This additional development effort is not worth the investment for the EHR vendor unless the third-party application has a significant market share.

Further, each third-party application developer would also have to support the single sign-on functionality on their end as well. And start-up companies and other small health IT vendors often struggle with supporting single sign-on technologies because of the complexity, resources, and costs involved. To address this issue, what is needed is an EHR vendor-agnostic solution that will help the IT Vendors achieve the same single sign-on integration without the involvement of the EMR vendor at a fraction of cost and fraction of time.

According to aspects of one embodiment of the present disclosure, one solution to this problems involves the development of a browser application (such as a Chrome application or Chrome app for the Google Chrome Browsers) that is made available as a browser extension (i.e., an application that extends the functionality of the browsers) through a web store (e.g., Chrome web store) that can be installed by EHR users for any of the web-based EHR systems that they may use. This application (e.g., a Chrome app) or browser extension will provide the EHR user with access to a button that can be clicked to launch the third-party application from the health IT vendor. By clicking the button, the EHR user directly logs into the health vendor's third-party application without a need for entering the credentials and also the EHR user logs into the same patient context as the patient the EHR user is accessing in the EHR system.

According to this embodiment, the EHR user is required to install the browser extension application (e.g., the Smartlink App) from the browser's respective store (such as the Chrome web store). After installing the browser extension application, the EHR user will log into the EHR application using the credentials provided by the EHR. By installing an application such as the browser extension application in the Chrome browser, the authenticated user provides the smart browser extension application the permissions to access the authenticated EHR pages. The browser extension application will then place a button (or link or other graphical user interface element) on one of the authenticated EHR web pages (this placement can optionally be determined by the clinic, a proxy identity provider such as Smartlink, and the IT vendor). When the EHR user is ready to launch the IT health vendor's third party web application, the EHR user will click on the launch button that is provided by the browser extension application on the EHR web page. When the user clicks the button (or initiates some other triggering or activation event on the browser extension), the browser extension application will access the patient information and the logged-in EHR user information that is available on the authenticated EHR web page and send the information to the health IT vendor. In this use case, the browser extension application will be acting as a proxy identity provider (or IdP). The EHR application is the one authenticating the EHR user, and so the health IT vendor will be a Service Provider (SP) that trusts the EHR user and validates the EHR user in their system. If the EHR user and the patient are present in the health IT vendor's third-part web application, it will send a successful response back to the proxy identity provider (e.g., Smartlink). If the EHR user and/or the patient are not present in the health IT vendor's system, it will be created in their system and send a successful response back. Once the proxy identity provider (e.g., Smartlink) receives a successful response it will initiate a Security Assertion Markup Language (SAML) assertion that includes both authentication assertion (contains EHR user information) and attribute assertions (contains patient information) that will be received by the health IT vendor. Once the health IT vendor receives the SAML assertion, the health IT vendor will create a login session for the EHR user and redirect the EHR user to their web page (in a separate tab in the browser) with the same patient context as that is in the EMR web page. In this use case, SAML is used as a single-sign-on protocol but the proxy identity provider (e.g., Smartlink) will be able to support other protocols like OAuth2 & OpenID connect.

FIG. 35 shows the sequence diagram for single sign-on using a browser application, such as a Chrome app, according to embodiments of the present disclosure. In FIG. 35, the single sign-on functionality 3500 is illustrated. A vendor such as Smartlink acts as the Identity Provider 3502, the EHR user installs the browser extension application (the Smartlink app) on a designated page in the EHR system 3504, and the health IT vendor acts as a service provider 3506. The sequence begins when the EHR user clicks the button in the browser when on the designated EHR web pages with the proxy identity provider (e.g., Smartlink) browser extension installed 3510. The proxy identity provider (e.g., Smartlink) sends the user information to the health IT vendor 3512. The IT vendor sends a successful response to the proxy identity provider (e.g., Smartlink) 3514. The proxy identity provider (e.g., Smartlink) then sends the SAML assertion and attribute assertion to the browser 3516. The browser relays the SAML assertions to the IT vendor 3518. The health IT vendor then responds with the requested resources 3520.

FIG. 36 shows the architecture diagram 3600 of the browser application according to embodiments of the present disclosure. The EHR user runs the proxy identity provider (e.g., Smartlink) extension on a desktop computer, laptop, notebook, tablet and the like, each device with its own respective operating system 3602 and installed browser application 3604 (such as the Google Chrome browser and the like). The browser 3604 can interact with both the EHR web site 3606 and the proxy identity provider (e.g., Smartlink) extension 3608. The EHR website 3606 has its own document object model (DOM) and associated scripts 3610 that control how the EHR web application works. The proxy identity provider (e.g., Smartlink) extension 3608 includes javascripts 3512 that are used in the operation of the browser extension. The proxy identity provider (e.g., Smartlink) extension can further interact with a browser's and system's application programming interfaces (APIs) 3614 in the case of granted privileges, obtaining almost the same rights as a browser. An extension works in the execution environment (the "content_scripts" key specifies a statically loaded JavaScript or CSS file to be used every time a page is opened that matches a certain URL pattern) also known as an isolated world where say inject JS code work within its environment and doesn't conflict with a websites JS functions.

FIG. 37 provides more detail on the architecture of the browser extension application 3608 according to embodiments of the present disclosure. The proxy identity provider (e.g., Smartlink) extension 3608 consists of a collection of files, packaged for distribution and installation. Browser extensions may include:

A manifest.json file 3702 that declares the extensions name, permissions, and what other components should be included.

A background script (optional—not shown in FIG. 37) that runs inside the browser and can access information such as web requests.

A content script (optional—not shown in FIG. 37) that runs inside pages that the EHR user loads, and can communicate with the background script.

A popup, opened with a toolbar button, that consists of a small web page loaded in the popup.

The manifest.json file 3702 is the only file that must be present in every extension. It contains basic metadata such as its name, version and the permissions it requires. It also provides pointers to other files in the extension. This manifest can also contain pointers to several other types of files:

Background pages 3704 which implement long-running logic.icons for the extension and any buttons it might define.

Content scripts 3706 which implement JavaScripts included with the extension that will inject into web pages. Popups, sidebars, and options pages, and HTML documents that provide content for various user interface components.

Another use of the proxy identity provider (e.g., Smartlink) browser extension is for the real-time the proxy identity provider (e.g., Smartlink) Data Connector (SDC). A key component of the embodiments disclosed herein include automation of patient record extraction and transmission utilizing various functionality with the EHR's graphical user interface (GUI) in bulk or one patient at a time. One drawback of using the GUI as the interface between two systems is not able to do the data processing real-time as this approach requires login into target system at a fix interval to process/move data because there is no access to source code or API (a command driven API can respond and act in real-time). Without the API, in practice, the shortest interval for the SDC may be 15 minutes to wake up and check of any data movement is needed. However, using the proxy identity provider (e.g., Smartlink) browser extension, it is possible to listen to any data changed in the source area, and automatically login into the target system and move the data will allow the use of SDC in real-time.

For example, when there are two different scheduling software systems managing the same clinic (one may be a partner who also need to schedule patient for the clinic), a 15 minute delay may cause double booking. But with the proxy identity provider (e.g., Smartlink) browser extension installed in the partner's scheduler, whenever there is a data change, it will automatically be synced to the clinic's scheduling system as well and avoid a duplicate booking for the same time slot.

The foregoing embodiments are presently by way of example only; the scope of the present disclosure is to be limited only by the claims.

The methods, systems, and devices discussed above are examples. Various embodiments may omit, substitute, or add various procedures or components as appropriate. For instance, in alternative configurations, the methods described may be performed in an order different from that described, and/or various stages may be added, omitted, and/or combined. Also, features described with respect to certain embodiments may be combined in various other embodiments. Different aspects and elements of the embodiments may be combined in a similar manner. Also, technology evolves and, thus, many of the elements are examples that do not limit the scope of the disclosure to those specific examples.

Having described several embodiments, various modifications, alternative constructions, and equivalents may be used without departing from the spirit of the disclosure. For example, the above elements may merely be a component of a larger system, wherein other rules may take precedence over or otherwise modify the application of the disclosure. Accordingly, the above description does not limit the scope of the disclosure. Embodiments of the present disclosure may be implemented as either software, hardware, or combinations therein.

The foregoing has outlined rather broadly features and technical advantages of examples in order that the detailed description that follows can be better understood. Additional features and advantages will be described hereinafter. The conception and specific examples disclosed can be readily utilized as a basis for modifying or configuring other structures for carrying out the same purposes of the present disclosure. Such equivalent constructions do not depart from the spirit and scope of the appended claims. Features which are believed to be feature of the concepts disclosed herein, both as to their organization and method of operation, together with associated advantages, will be better understood from the following description when considered in connection with the accompanying figures. Each of the figures is provided for the purpose of illustration only and not as a definition of the limits of the claims. Aspects of the embodiments of this disclosure are illustrated by way of example. While various details of one or more techniques are described herein, other techniques are also possible. In some instances, well-known structures and devices are shown in block diagram form in order to facilitate describing various techniques. A further understanding of the nature and advantages of examples provided by the disclosure can be realized by reference to the remaining portions of the specification and the drawings, wherein like reference numerals are used throughout the several drawings to refer to similar components. In some instances, a sub-label is associated with a reference numeral to denote one portion or part of a larger element or one of multiple similar components. When reference is made to a reference numeral without specification to an existing sub-label, the reference numeral refers to all such similar components.

What is claimed is:

1. A method of single sign-on using a browser extension application comprising:

receiving an activation event on an identity provider controlled browser extension application graphical user interface element rendered by a browser on a predetermined page on an electronic health record (EHR) web site with patient information and logged-in EHR user information;

sending the patient information and logged-in EHR user information captured from the predetermined EHR in response to the activation event to a health information technology vendor;

sending from the health information technology vendor system a successful response to an identity provider system associated with the identity provider controlled browser extension application;

sending from the identity provider system to the identity provider controlled browser extension application a Security Assertion Markup Language (SAML) authentication assertion and attribute assertion;

relaying, by the identity provider controlled browser extension application executing within the browser, the SAML authentication assertion and the attribute assertion to the health information technology vendor system; and responding from the health information technology vendor system with requested resources.

2. The method of claim 1, wherein the EHR web site has a document object model (DOM) and associated scripts that control how the identity provider controlled browser extension application graphical user interface element operates.

3. The method of claim 1, wherein the identity provider controlled browser extension application includes javascripts that are used in the operation of the identity provider browser extension application graphical user interface element.

4. The method of claim 1, wherein the identity provider controlled browser extension application interacts with application programming interfaces (APIs) in the case of granted privileges to obtain the same rights as a browser.

5. The method of claim 1, wherein the identity provider controlled browser extension application includes a collection of files which are packaged for distribution and installation.

6. The method of claim 1, wherein the identity provider controlled browser extension application includes a file that declares the extensions name and permissions.

7. The method of claim 1, wherein the identity provider controlled browser extension application includes a background script that runs inside the browser and can access information such as web requests.

8. The method of claim 1, wherein the identity provider controlled browser extension application includes a content script that runs inside pages that an EHR user loads and can communicate with background scripts.

9. The method of claim 1, wherein the identity provider controlled browser extension application includes a popup which is opened with a toolbar button that includes of a web page loaded in the popup.

10. The method of claim 1, wherein the identity provider controlled browser extension application includes metadata including name, version, permissions it requires, and pointers to other files in the identity provider controlled browser extension application.

11. The method of claim 1, wherein the identity provider controlled browser extension application includes pointers to several other types of files including background pages which implement long-running logic icons for the identity provider controlled browser extension application.

12. The method of claim 1, wherein the identity provider controlled browser extension application enables detection of data change in a source area and an automatic login to an EHR system to move the data in real time.

13. The method of claim 1, where if there is no corresponding information for either the patient information or the logged-in EHR user information recognized by the health information technology vendor system, then creating either the patient information or the logged-in EHR user information in the health information technology vendor system before responding from the health information technology vendor system with requested resources.

14. A method of single sign-on using an identity provider controlled browser extension application comprising:

receiving an activation event on an identity provider controlled browser extension application graphical user interface element rendered by a browser on a predetermined page on an electronic health record (EHR) web site that is concurrently displaying patient information and logged-in EHR user information;

sending the patient information and logged-in EHR user information captured from the predetermined EHR page in response to the activation event to a health information technology vendor system;

sending from the health information technology vendor system a successful response to an identity provider system associated with the identity provider controlled browser extension application;

sending from the identity provider system to the identity provider controlled browser extension application a Security Assertion Markup Language (SAML) authentication assertion and attribute assertion to the identity provider browser extension application graphical user interface element, wherein the SAML authentication assertion and attribute assertion are generated after receipt of the patient information;

relaying, by the identity provider controlled browser extension application executing within the browser, the SAML authentication assertion and the attribute assertion to the health information technology vendor system; and responding from the health information technology vendor system with requested resources.

15. A method of single sign-on using an identity provider controlled browser extension application comprising:

receiving an activation event on an identity provider controlled browser extension application graphical user interface element rendered by a browser on a predetermined page on an electronic health record (EHR) web site that is concurrently displaying patient information and logged-in EHR user information;

sending the patient information and logged-in EHR user information captured from the predetermined EHR page in response to the activation event to a health information technology vendor system, wherein the predetermined page is a non-login, patient-record page of the EHR system;

sending from the health information technology vendor system a successful response to an identity provider system associated with the identity provider controlled browser extension application, the identity provider controlled browser extension application being external to the EHR system;

sending from the identity provider system directly to the identity provider controlled browser extension application a Security Assertion Markup Language (SAML) authentication assertion and attribute assertion to the identity provider browser extension application graphical user interface element;

relaying, by the identity provider controlled browser extension application executing within the browser, the SAML authentication assertion and the attribute assertion to the health information technology vendor system without the EHR system participating; and responding from the health information technology vendor system with requested resources.

\* \* \* \* \*